(12) United States Patent
Anderson

(10) Patent No.: US 11,660,369 B2
(45) Date of Patent: May 30, 2023

(54) PHOTOCATALYTIC TITANIUM DIOXIDE COATING FOR LED LIGHT

(71) Applicant: Deloren E. Anderson, Crosby, MN (US)

(72) Inventor: Deloren E. Anderson, Crosby, MN (US)

(73) Assignee: DeLoren E. Anderson, Crosby, MN (US)

( * ) Notice: Subject to any disclaimer, the term of this patent is extended or adjusted under 35 U.S.C. 154(b) by 899 days.

(21) Appl. No.: 15/780,976

(22) PCT Filed: May 25, 2018

(86) PCT No.: PCT/US2018/034739
§ 371 (c)(1),
(2) Date: Jun. 1, 2018

(87) PCT Pub. No.: WO2018/218204
PCT Pub. Date: Nov. 29, 2018

(65) Prior Publication Data
US 2020/0282098 A1 Sep. 10, 2020

Related U.S. Application Data

(60) Provisional application No. 62/567,689, filed on Oct. 3, 2017, provisional application No. 62/511,679, filed on May 26, 2017.

(51) Int. Cl.
*A61L 2/08* (2006.01)
*A61L 9/20* (2006.01)
(Continued)

(52) U.S. Cl.
CPC ............. *A61L 9/205* (2013.01); *B01J 21/063* (2013.01); *B01J 35/004* (2013.01); *B01J 37/0215* (2013.01); *A61L 2209/12* (2013.01)

(58) Field of Classification Search
CPC ..... A61L 2/00; A61L 2/02; A61L 2/08; A61L 2/088; A61L 9/00; A61L 9/015;
(Continued)

(56) References Cited

U.S. PATENT DOCUMENTS 6,324,329 B1 11/2001 Mizuno
6,429,169 B1 8/2002 Ichinose
(Continued)

FOREIGN PATENT DOCUMENTS

WO WO-2017179082 A1 10/2017
WO WO-2018218204 A1 11/2018

OTHER PUBLICATIONS

"TiO2 Electron-Hole Recombination Equation", 2 pgs.
(Continued)

*Primary Examiner* — Natasha E Young
(74) *Attorney, Agent, or Firm* — Schwegman Lundberg & Woessner, P.A.

(57) ABSTRACT

A light includes a light emitting diode (LED) package to emit visible light, an electronics module coupled to the light emitting diode package, and a dome or fixture having a coating containing Photocatalytic Titanium Dioxide optically coupled to the light emitting diode package such that the coating containing Titanium Dioxide acts as a photocatalyst responsive to LED emitted light.

19 Claims, 21 Drawing Sheets

(51) Int. Cl.
*B01J 21/00* (2006.01)
*B01J 21/06* (2006.01)
*B01J 35/00* (2006.01)
*B01J 37/00* (2006.01)
*B01J 37/02* (2006.01)

(58) Field of Classification Search
CPC ..... A61L 9/04; A61L 9/12; A61L 9/16; A61L 9/18; A61L 9/20; A61L 9/205; A61L 2202/00; A61L 2202/10; A61L 2202/11; B01J 21/00; B01J 21/06; B01J 21/063; B01J 35/00; B01J 35/002; B01J 35/004; B01J 37/00; B01J 37/02; B01J 37/0215
See application file for complete search history.

(56) References Cited

U.S. PATENT DOCUMENTS

| | | | |
|---|---|---|---|
| 6,602,918 | B1 | 8/2003 | Ichinose |
| 7,913,859 | B2* | 3/2011 | Lai .......................... F21V 15/00 210/501 |
| 2009/0073686 | A1 | 3/2009 | Lai |
| 2009/0104086 | A1* | 4/2009 | Zax .......................... A61L 2/10 422/121 |
| 2013/0181246 | A1 | 7/2013 | Wu |
| 2013/0301274 | A1 | 11/2013 | Anderson |
| 2014/0211477 | A1 | 7/2014 | Anderson |
| 2015/0024925 | A1* | 1/2015 | Maclaughlin ............ B05D 3/12 502/158 |

OTHER PUBLICATIONS

Ichinose, Hiromichi, "Synthesis of peroxo-modified anatase sol from peroxo titanic acid solution", Journal of the Ceramic Society of Japan 104.1212, (1996), 715-718.

Yang, Xiujuan, "Different back electron transfer from titanium dioxide nanoparticles to tetra (4-sulfonatophenyl) porphyrin monomer and its J-aggregate", Chemical physics letters 334.4, (2001), 257-264.

"International Application Serial No. PCT/US2018/034739, International Preliminary Report on Patentability dated Dec. 5, 2019", 7 pgs.

"International Application Serial No. PCT/US2018/034739, International Search Report dated Aug. 24, 2018", 2 pgs.

"International Application Serial No. PCT/US2018/034739, Written Opinion dated Aug. 24, 2018", 5 pgs.

* cited by examiner

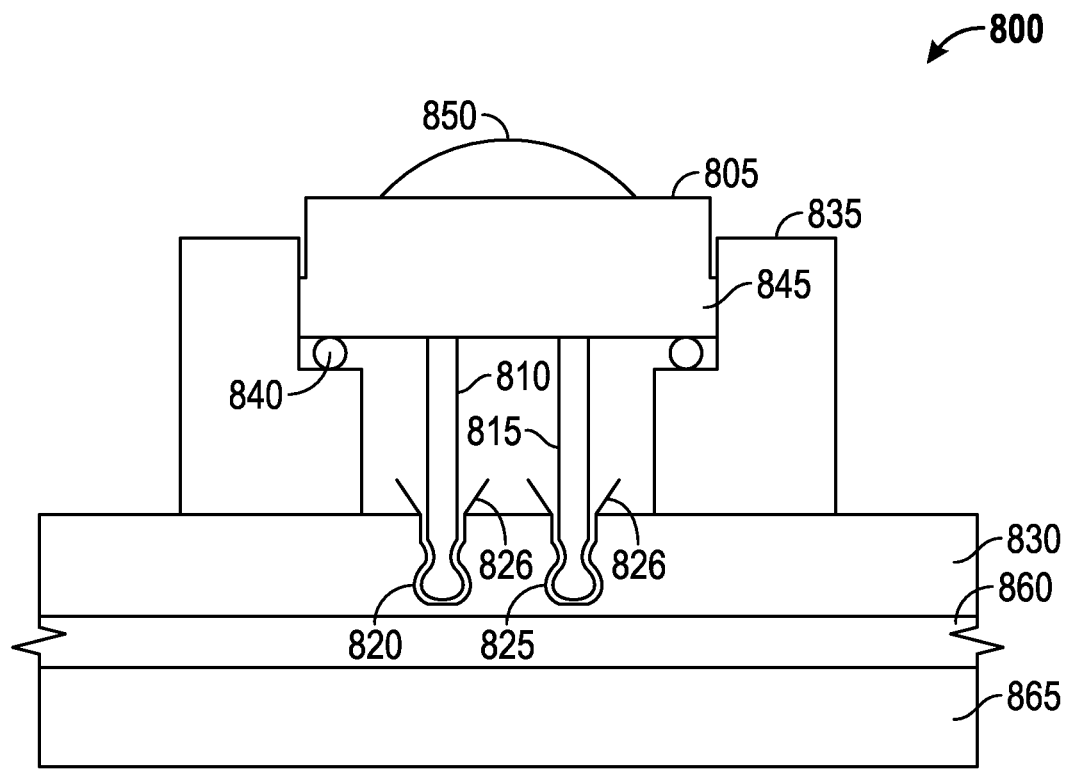
FIG. 8
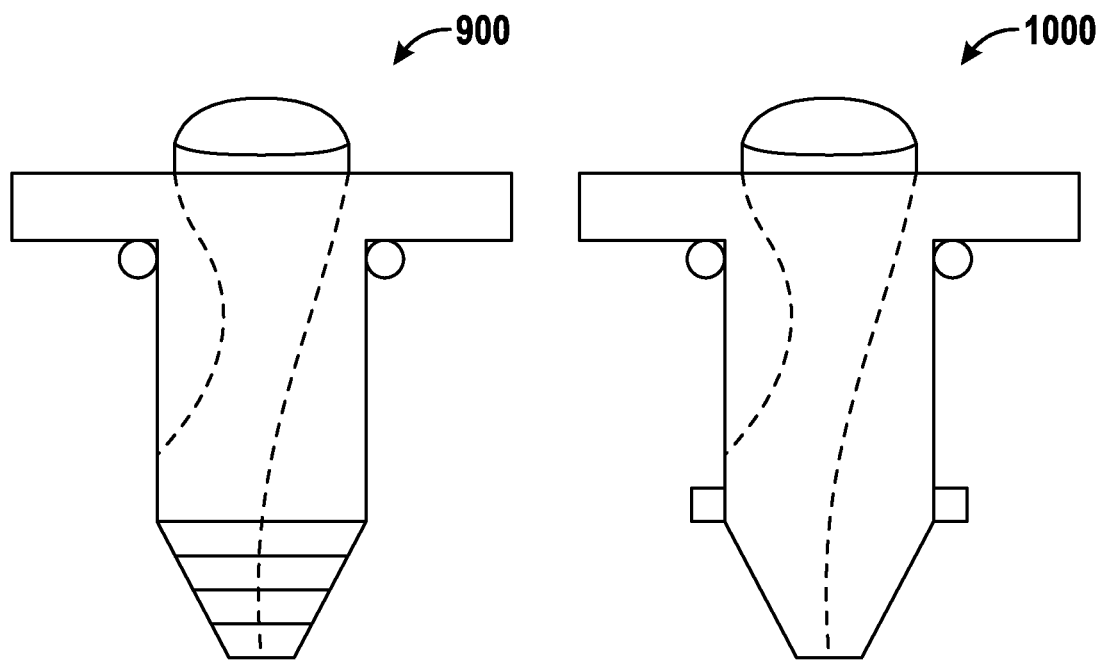
FIG. 9      FIG. 10

PHOTOCATALYTIC TITANIUM DIOXIDE COATING FOR LED LIGHT

PRIORITY APPLICATION

This patent application is a U.S. National Stage application under 35 U.S.C. 371 of International Application No. PCT/US2018/034739, now WO 2018/218704, filed on May 25, 2018, and published on Nov. 29, 2018, which claims priority benefit of U.S. Provisional Patent Application Ser. No. 62/511,679, filed May 26, 2017, and claims priority benefit of U.S. Provisional Patent Application Ser. No. 62/567,689, filed Oct. 3, 2017; the benefit of priority of each of which is hereby claimed herein, and which applications and publication are hereby incorporated herein by reference in their entirety.

BACKGROUND

Light emitting diodes have long been used individually or grouped together as background or indicating lights in electronic devices. Because of the efficient light production, durability, long life, and small size, light emitting diodes were ideal for electronic applications. Light emitting diodes are increasingly prevalent in a variety of lighting functions, including flashlights and various automotive uses.

BRIEF DESCRIPTION OF THE DRAWINGS

FIG. 8 is a block cross sectional view of a module supported in a socket according to an example embodiment.

FIG. 9 is a block cross sectional view of a module having a different connection mechanism to provide a sealed connection with a socket according to an example embodiment.

FIG. 10 is a block cross sectional view of a module having a different connection mechanism to provide a sealed connection with a socket according to an example embodiment.

DETAILED DESCRIPTION

Figure 1A:
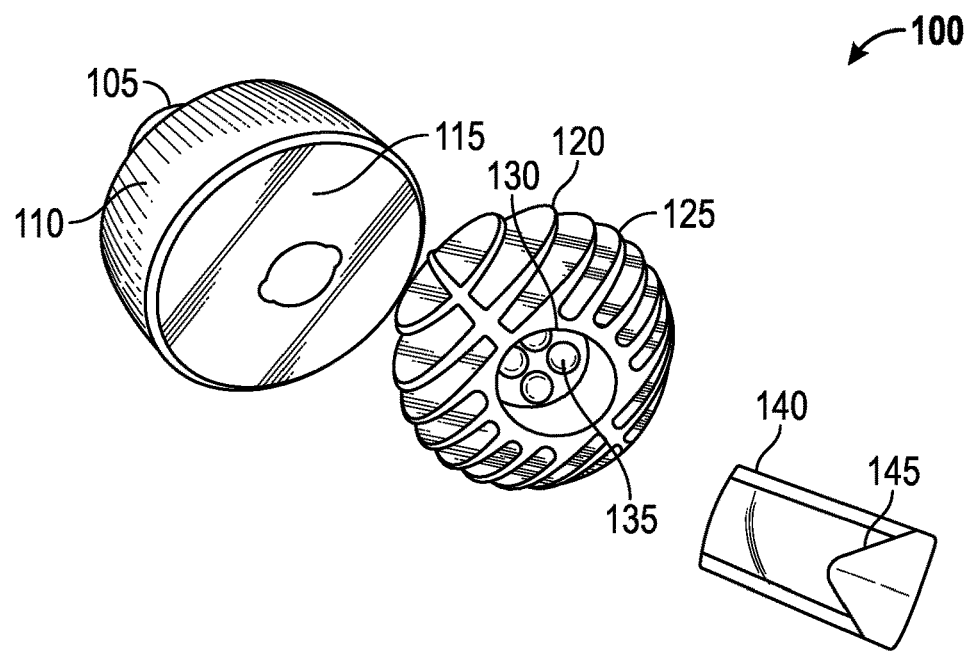
FIG. 1A is a view of a disassembled light emitting diode fixture, including a base module, a heat sink, and a lens according to an example embodiment.
Figure 1B:
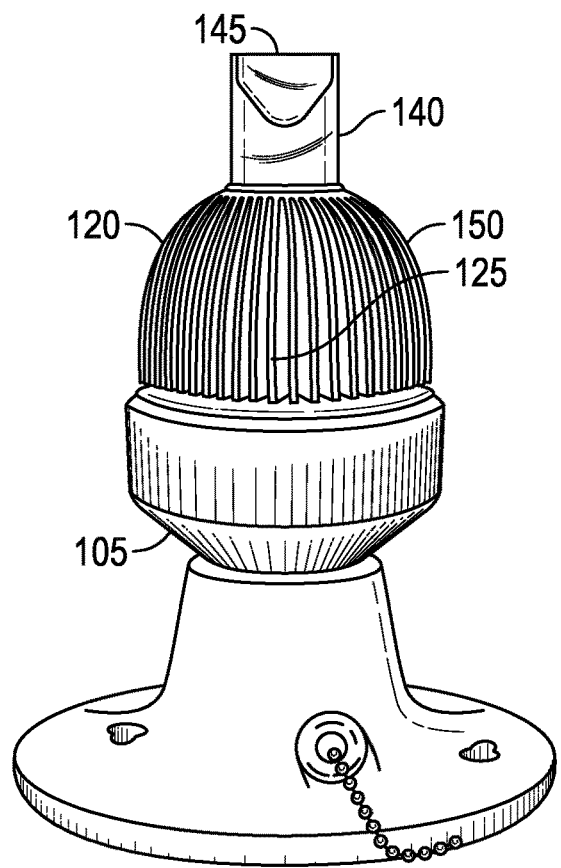
FIGS. 1B, 1C, 1D, and 1E illustrate further example heat sinks according to example embodiments.
Figure 1D:
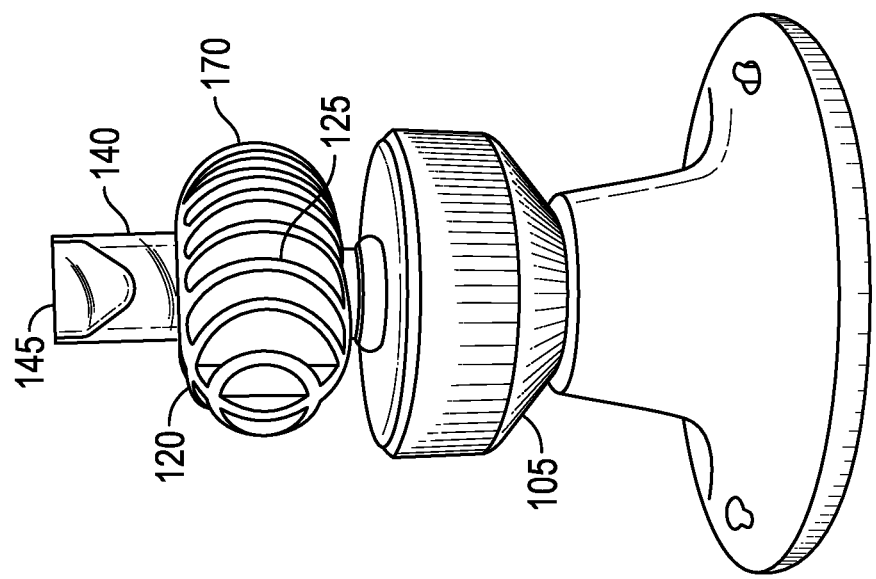
Figure 1C:
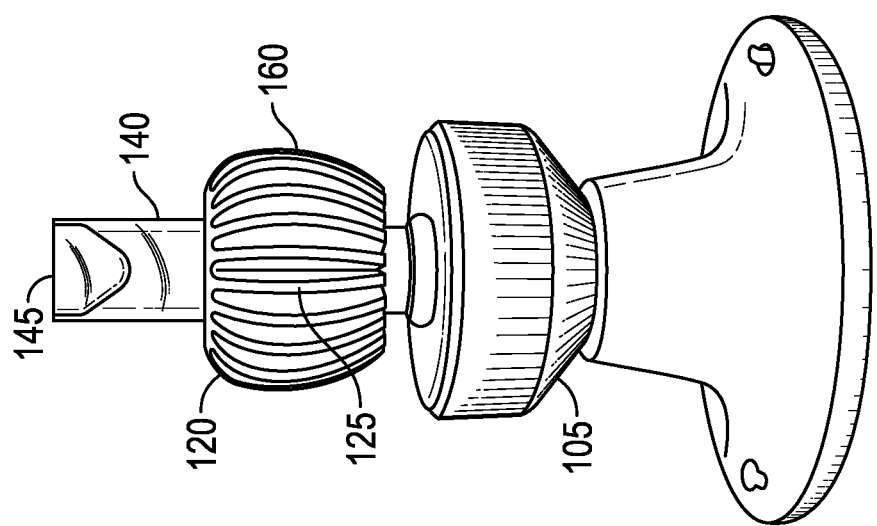

In the following description, reference is made to the accompanying drawings that form a part hereof, and in which is shown by way of illustration specific embodiments that may be practiced. These embodiments are described in sufficient detail to enable those skilled in the art to practice the invention, and it is to be understood that other embodiments may be utilized and that structural, logical, and electrical changes may be made without departing from the scope of the present invention. The following description of example embodiments is, therefore, not to be taken in a limited sense, and the scope of the present invention is defined by the appended claims. The present application describes embodiments of light emitting diode light fixtures.

In various embodiments, a light emitting diode light fixture can produce light for indoor areas, and may also produce a large volume of light for lighting large areas, such as parking lots, parking ramps, highways, streets, stores, warehouses, gas station canopies, and other locations. One or more light emitting diodes may be encapsulated into a substrate, such as a circuit board. The light emitting diodes may emit light of a specific color (e.g., wavelength) or specific color temperature (e.g., hue). For example, a light emitting diode may be red, green, yellowish white (2,700 K color temperature), bluish white (5,700 K color temperature), or other colors or color temperatures. In some embodiments, the substrate may be mounted on a cylindrical body portion to facilitate an electronic connection with an electronics module. The substrate and cylindrical body portion may be included within a cartridge. The cartridge may be mounted on or within a heat sink cooling structure. Some embodiments will mount the substrate at or near the end of the cartridge, where the end of the cartridge may be at or near the end of the heat sink to facilitate access to the substrate. To improve thermal diffusion, other embodiments may mount the cartridge near the center of mass of the heat sink, and use one or more lenses to focus light as described below. To improve light dispersion, one or more optical components may be mounted to surround the lens.

In some embodiments, Photocatalytic Titanium Dioxide is added to a diffuser to provide multiple characteristics. The Photocatalytic Titanium Dioxide may be added to the material during formation of the diffuser, and may also be added to an outside of the diffuser following diffuser formation. Photocatalytic Titanium Dioxide may operate as a catalyst on the outer light bulb shell made out of glass, Poly(methyl methacrylate) (PMMA), also known as acrylic or acrylic glass, or poly carbonate, but not to limited thereto. The outer light bulb shell may take many different shapes, such as bulbs, tubes, flat shapes, bell shape, cover, enclosing, encasing shapes and others.

In still further embodiments, Photocatalytic Titanium Dioxide may be added to fixtures holding the light emitting diodes. In portions of the fixture exposed to the emitted visible light in the 400 nm range or higher, as well as the Photocatalytic Titanium Dioxide coated diffuser, the Photocatalytic Titanium Dioxide acts as a photo catalyst for degradation of organic molecule pollutants. In one embodiment, the Photocatalytic Titanium Dioxide may be in the form of nanoparticles or crystals, which may be formed by extracting $TiO_2$ from peroxides and heating the particles to 250-260° C. The use of crystalline particles may both increase the surface area and hence photocatalytic efficiency of the Titanium dioxide and enable activation with visible light. In one embodiment, the crystalline particles are on average, less than 20 nm in diameter.

In one set of embodiments involving light emitting diodes with interchangeable components, the cartridges, heat sinks, lenses, or optical component may be individually replaceable. Individually replaceable components may avoid the need to replace an entire fixture. For example, if the light emitting diode or electronics within the cartridge fails, the cartridge may be replaced without requiring replacement of the lens. Additionally, the cartridges, heat sinks, lenses, or optical components may be manufactured to facilitate replacement by a user. For example, the lens may slide within the cartridge, the cartridge and lens may slide within the heat sink, and the lens may be mounted on the heat sink. The components may be mounted using a friction fit, where the friction fit enables user replacement of components, but is also secure enough to maintain the fixture structure.

Figure 1E:
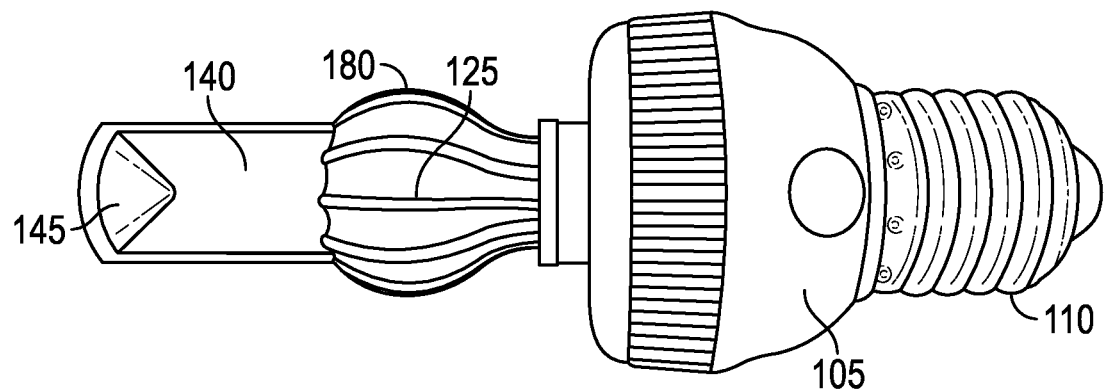

FIG. 1A illustrates one light emitting diode fixture 100. The base 105 has an Edison style connector 110 (seen more clearly in FIG. 1E) for mating with a light socket, electronics for driving the light emitting diode, and a socket 115 for mating with a substrate or heat sink 120. Connector 110 in one embodiment is an Edison 27 mm male screw base. In one embodiment, the electronics include a driver suitable to drive light emitting diodes at a current of approximately 700 mA, or in further embodiments between 350 to 1000 mA. The light emitting diode may draw approximately 9 watts at this current, yet produce light equivalent to a 100-watt incandescent light bulb. The parameters for current draw and watts are for one particular example. The current and wattage may vary significantly in further embodiments and as new light emitting diodes and driver circuitry evolve. The number of light emitting diodes utilized may also vary significantly, from one to more than four in various embodiments.

The heat sink 120 in one example has a plurality of fins 125 extending laterally from a depression 130 to dissipate heat away from the substrate or light emitting diodes. Because the light fixture 100 may be used for indoor or outdoor applications, some embodiments are able to withstand a large ambient temperature range and inclement weather conditions while still efficiently emitting light. The heat dissipating fins 125 draw heat away from the light emitting diode to prevent damage to the light emitting diode or the surrounding components. In one embodiment, the heat dissipating fins 125 may be reflective to improve light dispersal. The heat dissipating fins 125 may be manufactured using a reflective material, or may be coated with a reflective material. The reflective surfaces may also reduce the amount of light absorbed by the surface of the heat dissipating fins 125, thereby improving the heat dissipating properties of the heat sink 120.

Further embodiments of the heat sink are illustrated at 150, 160, 170, and 180 in FIGS. 1B, 1C, 1D, and 1E, respectively. Many other designs of heat sinks designed with varying amounts of surface area and space between fins or other heat convection surface to convey heat away from the light emitting diode or diodes may be utilized in further embodiments. Many have laterally extending plates or fins from a central core designed to absorb heat from the light emitting diodes. In yet further embodiments, different types of heat sinks may be utilized, such as a tube with a liquid that vaporizes and transports heat away from the heat source until it condenses, releasing heat to ambient away from the light emitting diode. The liquid may be thought of as a refrigerant, and in various embodiments, may use gravity to transport the condensed liquid back toward the heat source. The liquid should be selected to boil at temperatures expected from the light emitting diodes, yet not solidify at expected ambient operating temperatures. Still further heat sinks may be utilized in further embodiments.

The base 105 or heat sink 120 may be manufactured using aluminum or copper to provide both strength and heat dissipation to moderate the substrate temperature. The base 105 or heat sink 120 may be manufactured using a reflective material such as a polished metal, or may be coated with a reflective material such as zinc, tin, copper, silver, or other materials. The reflective material may be used to improve light dispersion and heat dissipation. The substrate may be integrated with the heat sink 120 and provide feed through electrical conductors to the light emitting diodes.

In one embodiment, heat sink 120 may be designed to accommodate a removable and replaceable light emitting diode substrate. The heat sink 120 may itself have one of several different light fixture connector types, including but not limited to Edison type connections, bayonet-type connections, or snap-in or friction connections.

The heat sink depression 130 may extend to the middle of the heat sink in some embodiments to facilitate heat dissipation. The depression 130 may hold the substrate, light emitting diodes, and optical component 135 at the bottom of the depression. In some embodiments, the depression 130 may extend only marginally into the heat sink, since much of the heat generated by the LEDs is radiated from a bottom of the substrate, opposite the direction of light emission. The optical component 135 focuses light away from the substrate and directly out of the heat sink 120. The substrate is thermally coupled to the walls of the depression 130 within the heat sink 120. The light emitting diodes are electrically coupled to the substrate, and the substrate is electrically coupled to the electronics within the base 105.

The optical component 135 coupled to the light emitting diode may provide a protective seal. The optical component 135 may be placed on and adhered to a filling material surrounding the actual light emitting diode. As the filling material solidifies, the optical component 135 may be securely fastened to the filling material.

In one example embodiment, the depression 130 may be cylindrical, and extends a sufficient distance into the heat sink to support a lens 140. The lens 140 is optically coupled to the optical component 135. In some embodiments, a gel may be disposed between the lens 140 and the optical component 135 to facilitate transfer of light from the optical component 135 to the lens 140. The gel may provide a watertight seal and protect the electrical connections from moisture or dirt that might degrade the electrical contact formed by such connections. In further embodiments, the gel operates to provide a seal over a wide depth of compression.

In one embodiment, the lens 140 may be cylindrical or have a polygonal cross section, fits within the depression 130, which may also have a cylindrical or polygonal cross section. The lens 140 may be adhered by a sealant between the lens 140 and the depression 130. The lens 140 may be a plastic rod, a glass rod, or a cylinder of another transparent or translucent material suitable for transmission and focusing of light. The lens 140 has a divot 145 on the end opposite from the optical component 135, and the divot is used to disperse light omnidirectionally. The divot 145 may be a conical shaped bore, and the walls of the bore may reflect light from within the lens in a 360-degree dispersal pattern about the lens. The divot 145 may have a pointed or rounded tip. The lens 140 or divot 145 may be substantially transparent, or may be coated with a translucent or colored material to soften the light emitted from the fixture. The lens 140 has a divot 145 may be formed using injection molding, or may be formed using precision glass molding or glass grinding and polishing.

In some embodiments, the divot may have an angulated point, and may have many facets, such as a four or more to obtain a desired pattern of light reflection. In some cases, the divot 145 may provide for reflection about a selected angle such as between 90 to 360 degrees. In one embodiment, the divot 145 may provide for a reflection that directs a portion of the light toward the reflective heat sink 120, where the reflective heat sink surface disperses light. To improve dispersal of light from the divot, the reflective heat sink core may have a greater diameter at the base than at the end away from the base. In further embodiments, a multifaceted divot may be used to obtain selected light patterns.

Many different types and shapes of lenses may be used. For large area high intensity lighting applications, the lens may be shaped to provide directional lighting, or a widely dispersed beam of light such that when all the modules in an array are properly oriented, a desired pattern of light is provided to light a large area, such as a parking lots, parking ramps, highways, streets, stores, warehouses, gas station canopies. Similarly, different lenses may be used for many different applications, such as for forming spotlights, narrow beams from each module may be desired.

In further embodiments, the substrate may be a simple circuit board or other suitable material for supporting light emitting diodes. The substrate may be fixed into the heat sink with adhesive or mechanical means of securing the substrate and thermally coupling it to the heat sink. Wires may be provided to couple the light emitting diodes to the driver circuitry in the base 105. In this embodiment, the light emitting diode portion of the light fixture is not easily removable by a consumer.

In still further embodiments, the light emitting diodes may be formed in, or coupled directly into the lens 140, such that light is directly coupled to the lens, with a back side of the light emitting diodes positioned when assembled to conduct heat directly to the heat sink. The rod at the end proximate the light emitting diodes may also be shaped to facilitate light transmission from the light emitting diodes directly into the rod without the need for further optical components.

In some embodiments, a light emitting diode module may be utilized with a desired number of light emitting diodes. The module may be mounted on a substrate with an integrated heat sink, such as a plate that may be thermally coupled to the heat sink 130. The light emitting diode module may also contain an integrated lens to direct light away from the light emitting diode. This module may be embedded directly into the end of the lens, which may be formed by injection molding, or cut from rod stock in various embodiments. Further methods of forming the lens may be used, as well as different methods of optically coupling the light emitting diode or light emitting diode module to the lens and to the heat sink.

Figure 1F:
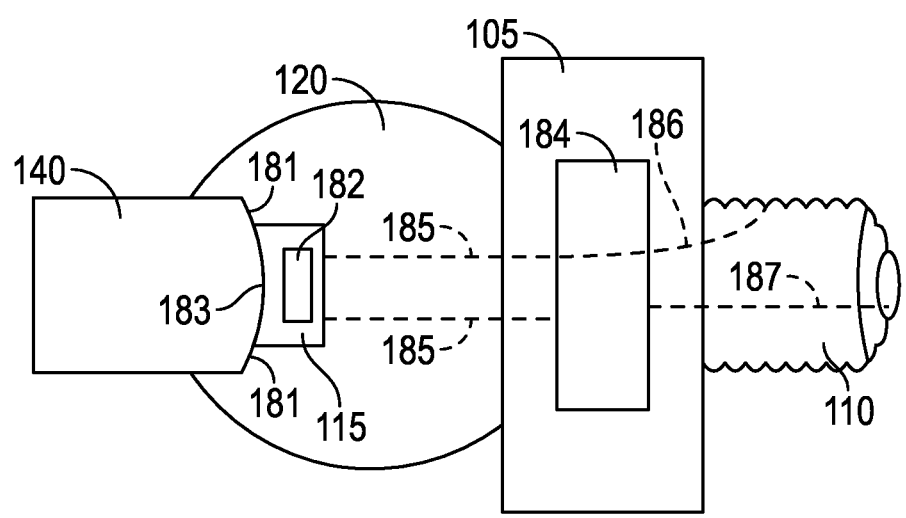
FIG. 1F is a cross sectional representation of a further light emitting diode fixture according to an example embodiment.

FIG. 1F is a cross section representation of a further light emitting diode fixture according to an example embodiment. In this embodiment, a ledge 181 is provided in the opening 115 to support the rod 140 a selected distance above a light emitting diode module 182. In one embodiment, the rod 140 has a convex shape on an end 183 of the rod proximate the light emitting diode module 182. The rod 140 is positioned by the ledge 181 to receive light and transport light toward the other end of the rod.

Standardizing the position of the rod 140 with respect to the light emitting diode module 182 allows the elimination of additional optical elements and optical gel to capture light from the light emitting diode module 182 into the rod 140. In one embodiment, the ledge 181 along with the curvature of the convex end 183 of the rod 140 is selected to provide consistent spacing from light emitting diode module 182 to capture the light from the light emitting diodes.

Many different length rods 140, and rods 140 with many different light dispersal mechanisms, may be used. The end of the rod 140 distal to the light emitting diode module 182 may include a dimple in some embodiments to provide light like a standard incandescent light bulb, with a center of light consistent with current standard 40, 60, and 100 watt bulbs if desired. The rod may also be shaped with a concave or convex surface to provide an emitted light dispersal pattern consistent with spot or floodlights in further embodiments. Simply utilizing a different rod for a different light dispersal pattern provides a simple, flexible way to adapt the light fixture to many different applications currently done with other types of lighting. For example, shorter rods with selected end characteristics may be used for streetlight or flood light applications. In some embodiments, the rods may be interchangeable, either by the consumer or during manufacture with little process change. An interchangeable rod may be replaced with a rod that provides a different light dispersion pattern. An interchangeable rod also enables a user to access other components, thereby facilitating replacement of the electronics package, the heat sink, or the optical component. Simply using the existing heat sink with ledge and electronics package provides great flexibility in solving many different lighting needs.

FIG. 1F also illustrates electrical connections between the light emitting diode module 182 and an electronics package 184 in the base 105 that includes a driver for the light emitting diode module 182. Wires 185 may be positioned via a through hole in the heat sink 120 to contact the electronics 184, which may be further coupled via wires 186 and 187 to the connector 110.

In one embodiment, the rod may be about 22 mm in diameter, and the ledge 181 may be approximately ½ mm. Other dimensions may be utilized in different embodiments. The curvature of the convex end 183 of the rod 140 may be approximately 3/16ths to 1/8 inches in one embodiment, and may vary significantly in further embodiments. The curvature and length between the end 183 and the light emitting diode module 182 may be selected to optimize optical coupling of the rod 140 and light emitting diode module 182. In further embodiments, the light emitting diode module 182 may also include one or more lenses.

Figure 2A:
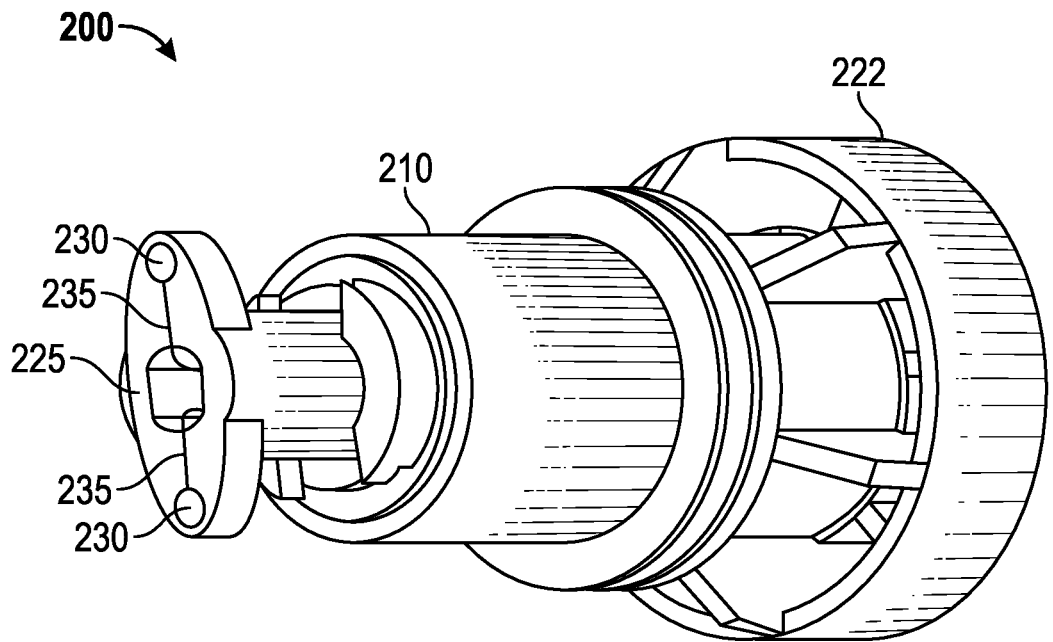
FIGS. 2A-2B illustrate perspective views of a light module and various aspects of a light fixture that uses replaceable light modules according to example embodiments.
Figure 2B:
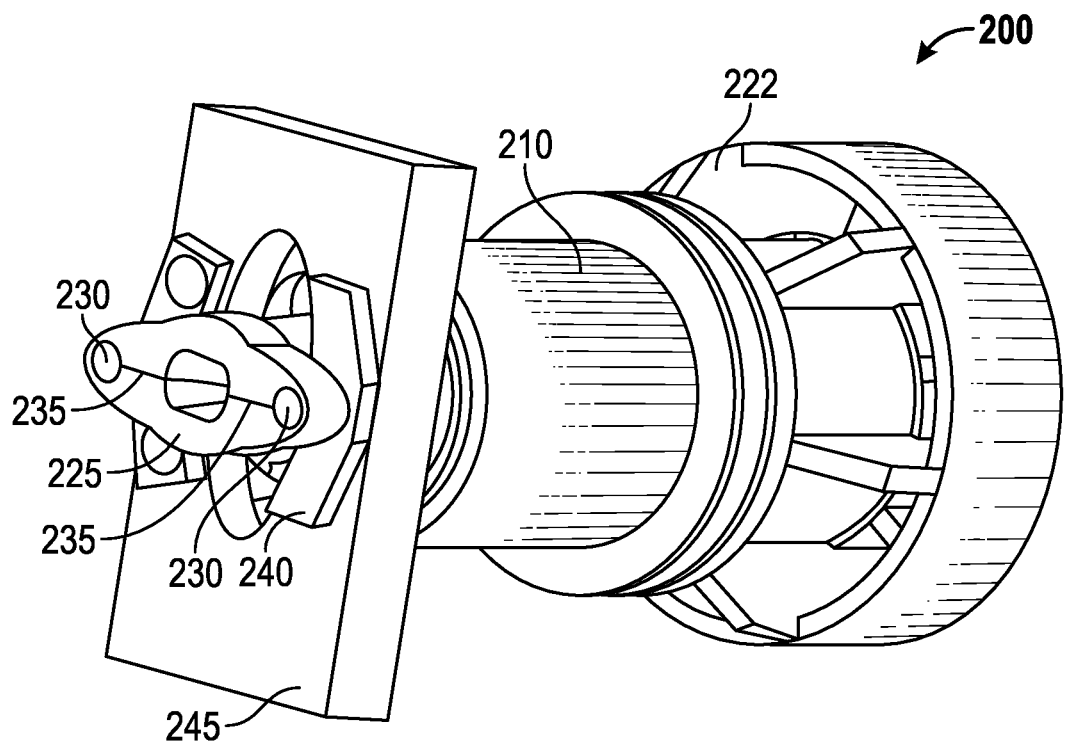

FIGS. 2A-2B illustrate an LED light module substrate 200 having a body portion 210. Body portion 210 may be cylindrical, or have a polygonal cross section, and may be formed of metal, such as aluminum, copper, or other heat conducting materials, and may have a heat sink portion formed on one end with fins 222 or other structures to facilitate conduction of heat away from an LED supported by the module 200 at the same end. Body portion 210 or fins 222 may be manufactured using a reflective material such as a polished metal, or may be coated with a reflective material such as zinc, tin, copper, silver, or other materials. The reflective material may be used to improve light dispersion and heat dissipation. Body portion 210 may be formed of glass, where the glass may improve light dispersion by transmitting or reflecting light.

A second end of the substrate body portion 200 may include a foot 225 spaced apart from the body portion and at least partially formed of an electrically insulating material. Foot 225 is formed in an oval shape in one embodiment, with contacts 230 positioned at both ends of the oval shape. In one embodiment, the contacts extend to the side of the foot that is not shown, but is facing the body portion 210. When the foot 225 is inserted through the heat sink depression 130 into the base socket 115 (shown in FIG. 2B as a plane 245) and twisted into position, it brings the contacts 230 into good electrical connection with power contacts 240 to supply power to the module 200 from the driver electronic in base 105. Conductors 235 may be coupled to contacts 240 and fed through an opening in the foot 225 back through the body portion to supply power to the LED.

Figure 2C:
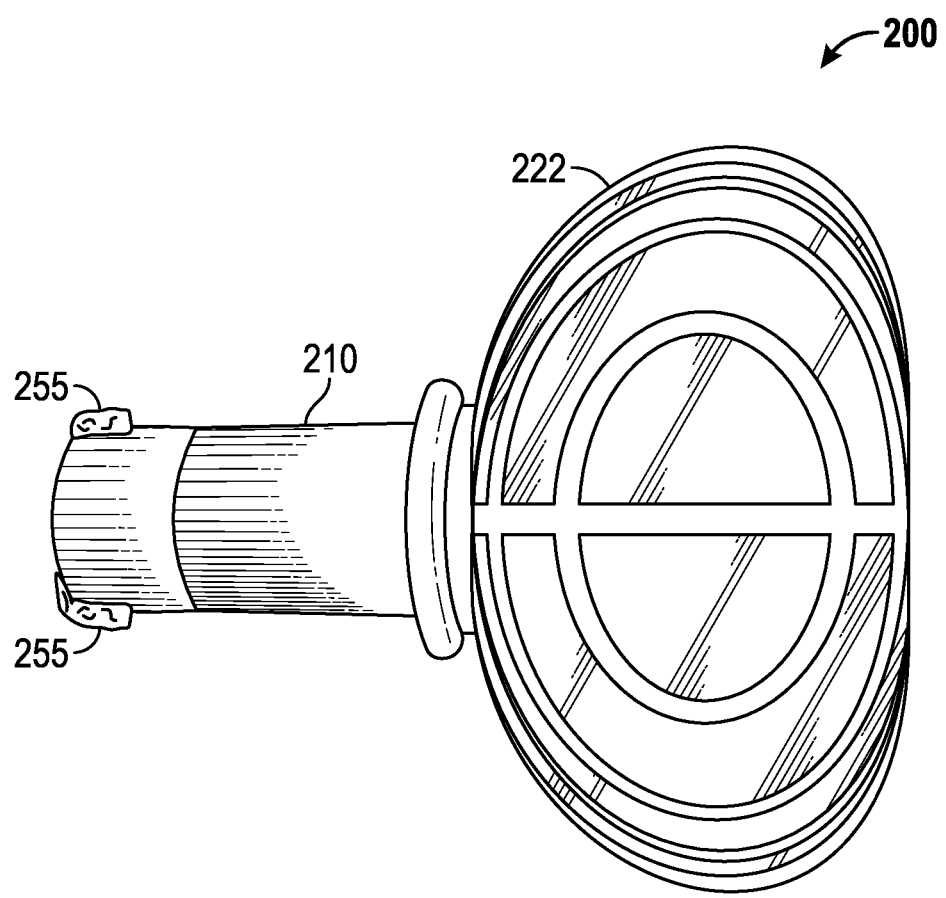
FIG. 2C is a perspective view of an alternative light module according to an example embodiment.

In further embodiments, as shown in FIG. 2C, an alternative foot is illustrated as small projections 255 with contacts that connect with power contacts 240 to supply power to the module 200.

The substrate is inserted in the socket 115 on the base 105, then turned into position as to align the contact points 230 with power contacts 240 to couple to the driver electronics. The pressure on the contact points 230 may be developed from a compression fit against spring-loaded contacts, or via compression of washer or other feature in various example embodiments. The inside of the base 245 creates extensive pressure between contact points 230 and power contacts 240, ensuring reliable electrical contact through a wide range of expansion or contraction of the fixture.

Figure 3A:
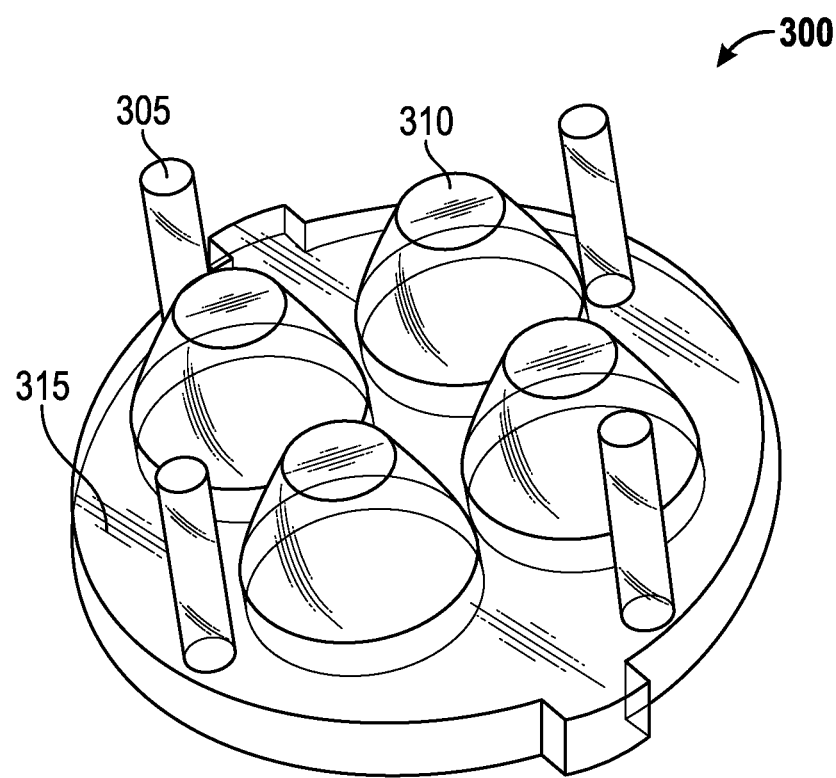
FIG. 3A is a bottom view of an optical component to direct light away from light emitting diodes.
Figure 3B:
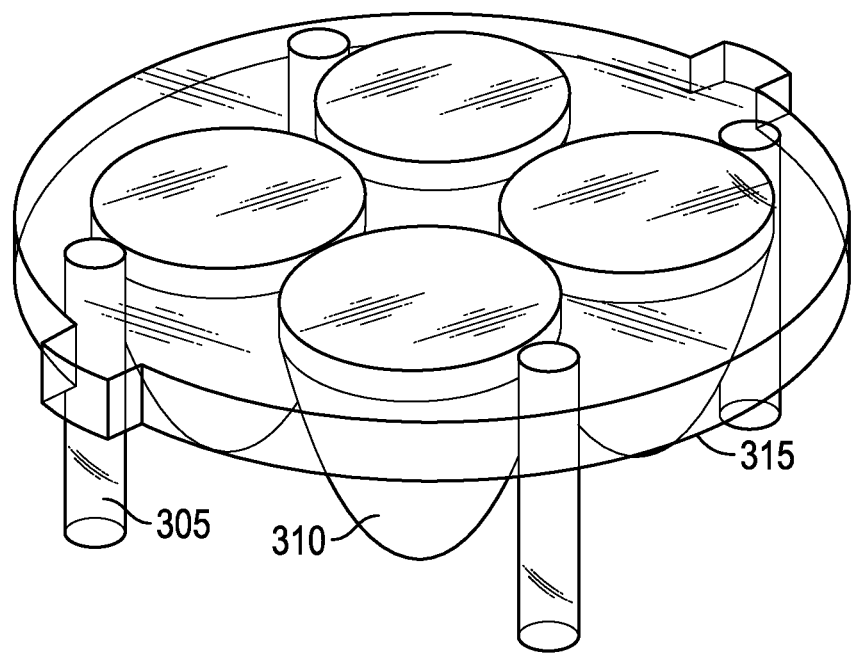
FIG. 3B is a top view of an optical component to direct light away from light emitting diodes.

FIGS. 3A-3B illustrate an optical component 300 that may be used to focus light from the light emitting diodes away from the substrate. FIG. 3A illustrates the optical component 300 from the LED-facing bottom side, and FIG. 3B illustrates the top of the optical component 300. This optical component 300 may have posts 305 that may be used to support the optical component 300 above a light emitting diode substrate, or that may be used to mount the substrate to post holes on the light emitting diode substrate. The optical component 300 has smaller, substantially conically shaped elements 310 that focus light from each light emitting diode directly away from the light emitting diode substrate. The support posts 305 and cones 310 are connected to a disc 315 to maintain their configuration, and to allow the optical component to be replaced as a single unit.

In various embodiments, one or more light emitting diodes may be positioned on the substrate with one or more cones 310 corresponding to each light emitting diode, or a single cone 310 may be formed over more than one light emitting diode to help couple light into the rod 145.

In one embodiment, the base, heat sink, substrate, light emitting diodes, optical component, and lens may be replaced as a single unit. In another embodiment, the base, including driver electronics and heat sink may form one component, and the substrate, light emitting diodes, optical component, and lens may form a second component. In other embodiments, each of the heat sink, substrate, light emitting diodes, optical component, and lens may be replaced separately. The ability to replace components separately can be desirable, such as if the mean time between failures for one component is significantly shorter than for another component. The ability to select different lenses can also be beneficial for different lighting needs of a consumer. In some embodiments, the components may be assembled using a friction fit that renders them easily replaceable by a consumer. In further embodiments, all the components may be assembled in a manner that renders them not easily replaceable by a consumer, such as in industrial lighting applications.

Figure 4:
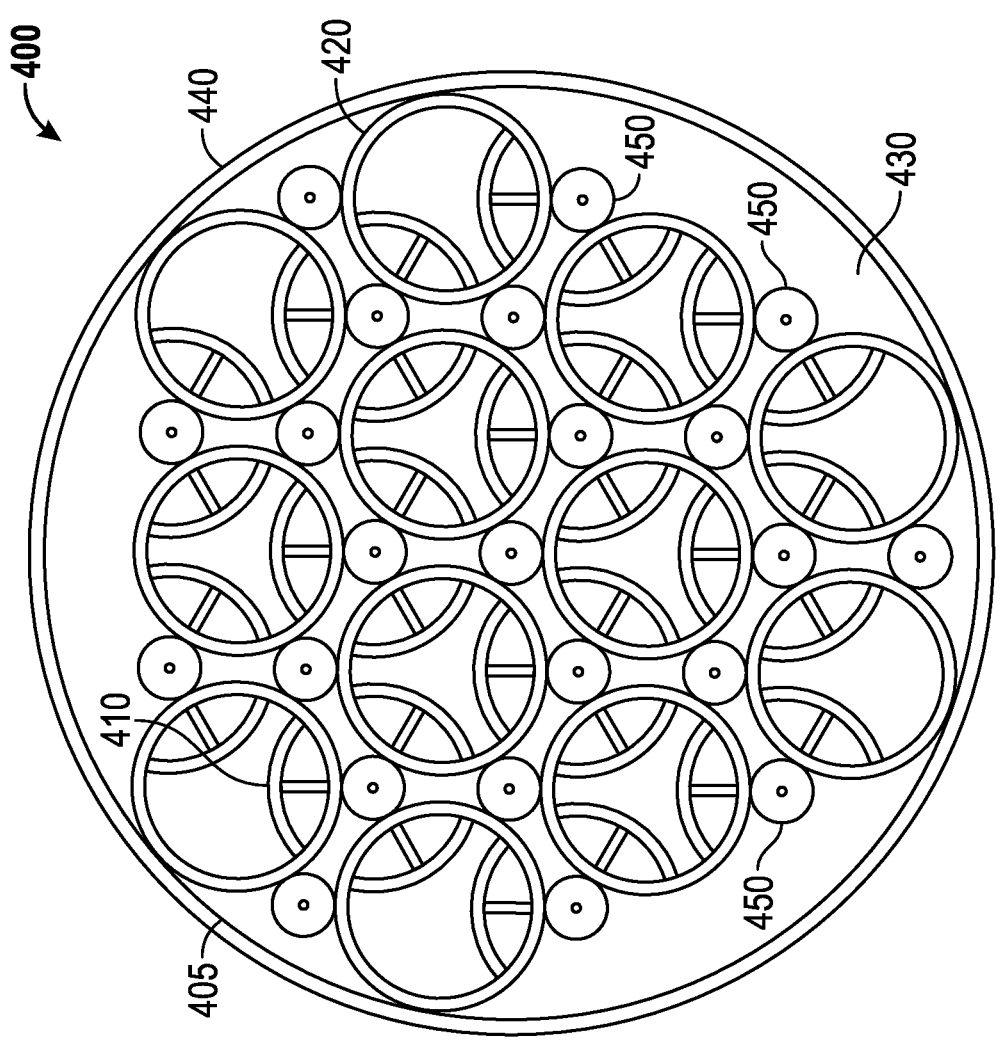
FIG. 4 is a top view of a matrix of light emitting diode modules according to an example embodiment.

FIG. 4 is a top view of light fixture 400, which includes a rigid substrate that arranges the light emitting diode modules into a matrix 405. Multiple LEDs may be encapsulated into modules 410, which may be seen in FIG. 4 through cylindrical cooling structures 420. In this view, the modules provide light pointing away from the surface of the figure.

In one embodiment, the cooling structures 420 and modules 410 are supported by the LED matrix 405, which may be formed of aluminum in one embodiment to provide both strength and heat conduction to help keep the modules 410 cool. In one embodiment, the LED matrix 405 may be formed of glass to provide strength, heat conduction to help keep the modules 410 cool, and low thermal expansion. A board 430, such as a circuit board, may be placed integrated with the cooling structures 420 and provides appropriate feed through electrical conductors between the modules 410. In one embodiment, board 430 may be a standard circuit board with metallization for forming the conductors. In one embodiment, a frame 440 may be formed around the matrix and be integrated with the matrix.

The matrix and cooling structures 420 may be formed of aluminum, copper, or other material that provides adequate structural support, is lightweight, and conducts heat well. The matrix and cooling structures 420 may be formed of a reflective material such as a polished metal, or may be coated with a reflective material such as zinc, tin, copper, silver, or other materials. The reflective material may be used to improve light dispersion and heat dissipation. In one embodiment, the matrix and cooling structures 420 may be formed of glass to provide strength, heat conduction, and low thermal expansion. A plurality of electrical sockets 450 may be formed on the matrix between the cooling structures and are secured to the board 430 in one embodiment, forming a matrix of electrical sockets 450 that may be electrically interconnected in two dimensions by the board 430. One or more light emitting diode modules 410 may be individually removable and replaceable within any individual electrical socket within the matrix, and one or more lenses may be mounted to each of the light emitting diode modules 410. In one embodiment, a combination of light emitting diode modules 410 of different color temperatures may be chosen to provide a desired color combination. For example, a combination of yellowish white (2,700 K color temperature) and bluish white (5,700 K color temperature) light emitting diode modules 410 may be used in a matrix to provide a white (e.g., 4,300 K color temperature) light. During replacement of light emitting diode modules 420, the lens may be removed from a failed light emitting diode module and mounted to a replacement light emitting diode module. One or more light emitting diode modules 410 may be rigid in one embodiment and may be secured within the matrix 405 by an epoxy or other filler material having suitable heat conducting and retentive properties to ensure the board 430 is securely held in place over the sockets 450.

As may be seen in FIG. 4, more sockets than can accommodate modules may be provided in various patterns. The additional sockets provide flexibility for a multitude of lighting needs. In one embodiment, the sockets may provide for the use of an optimum number of modules to provide a high volume of lighting for outdoor applications, such as parking lots, parking ramps, highways, streets, stores, warehouses, gas station canopies. For lower volume lighting applications, fewer modules may be used in fewer sockets. For each configuration of sockets with modules, the electrical connections may be modified to provide a proper voltage for each module.

Figure 5A:
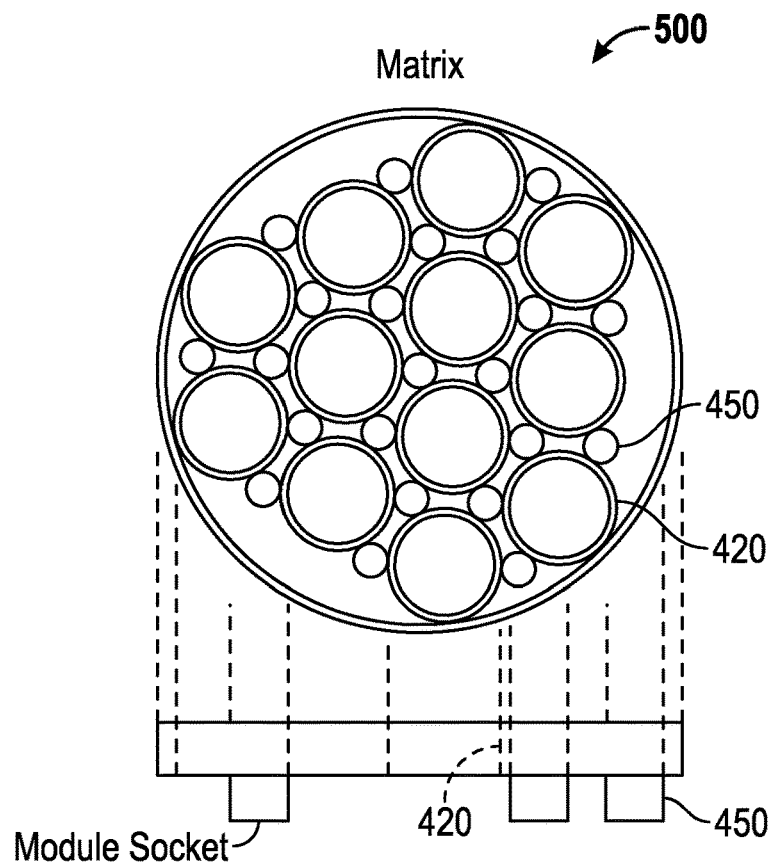
FIG. 5A is a top view of a matrix including sockets for light emitting diode modules according to an example embodiment.

FIG. 5A is a top view of matrix 405 including sockets 450 for light emitting diode modules according to an example embodiment. As shown, the matrix 405, with cooling structures 420 and sockets 450 that may have some depth to them that provides structural support, may be formed of heat conducting material. The sockets are disposed between the cooling structures such that heat is easily conducted to the cooling structures.

Figure 5B:
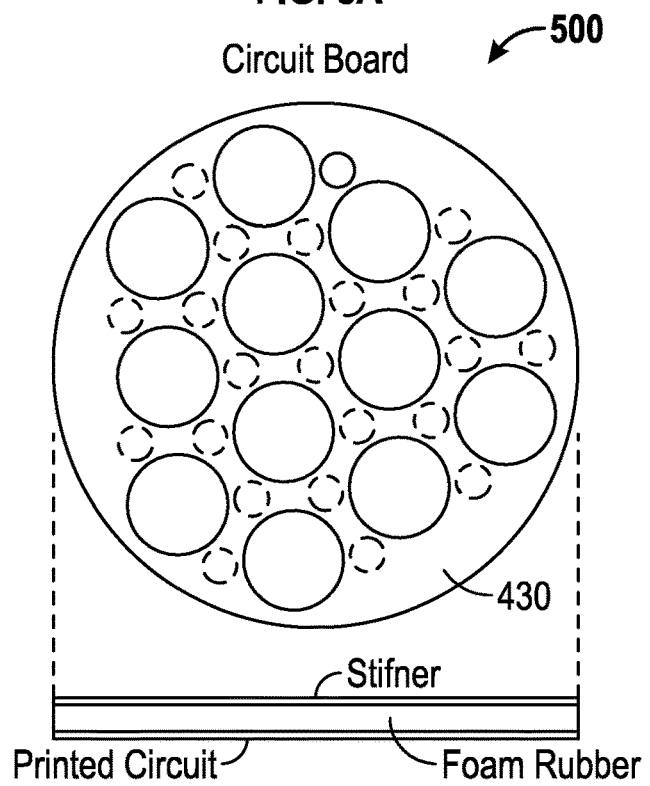
FIG. 5B is a top view of a circuit board for mating with the matrix of FIG. 2B according to an example embodiment.

FIG. 5B is a top view of circuit board 430 for mating with the matrix of FIG. 5B according to an example embodiment. The board 430 has openings corresponding to cooling structures 420 in one embodiment, and sets of connectors corresponding to the sockets when coupled to the matrix.

Figure 6:
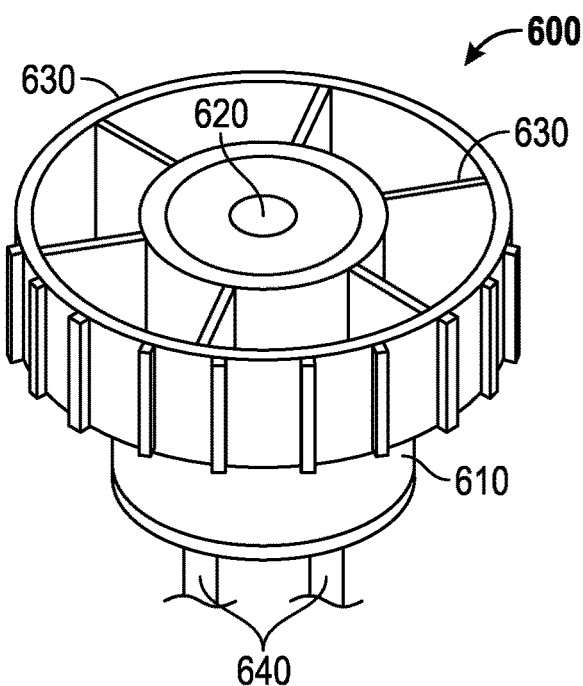
FIG. 6 is a perspective view of a high intensity light emitting diode module according to an example embodiment.

Each individual light emitting diode module as shown in further detail at 600 in FIG. 6 may include a base 610 and a light emitting diode 620. The base may be configured and arranged for fitted electrical engagement within the electrical socket 450. Light emitting diode modules 600 may fit in the electrical sockets 450 through multiple different types of connections. In various embodiments, the light emitting diode 620 may be different colors with most colors being currently commercially available.

The base 610 of the light emitting diode module 600 may include heat dissipating radial fins 630 to dissipate heat away from the electrical socket 450 and leads or contacts 640 for coupling to connectors on board 430 for providing power to the light emitting diode 620. Because the light emitting diode module 600 may be used for both inside and outside applications, some embodiments are able to withstand a large ambient temperature range provided it is not too warm for proper operation, and may also withstand inclement weather conditions including rain, snow, ice, dust, winds, while still efficiently emitting light. The heat dissipating fins 630 may extend radially from a top of the base 610, drawing heat away from the light emitting diode 620, and acting as a heat sink to prevent damage to the light emitting diode or the surrounding components.

Figure 7:
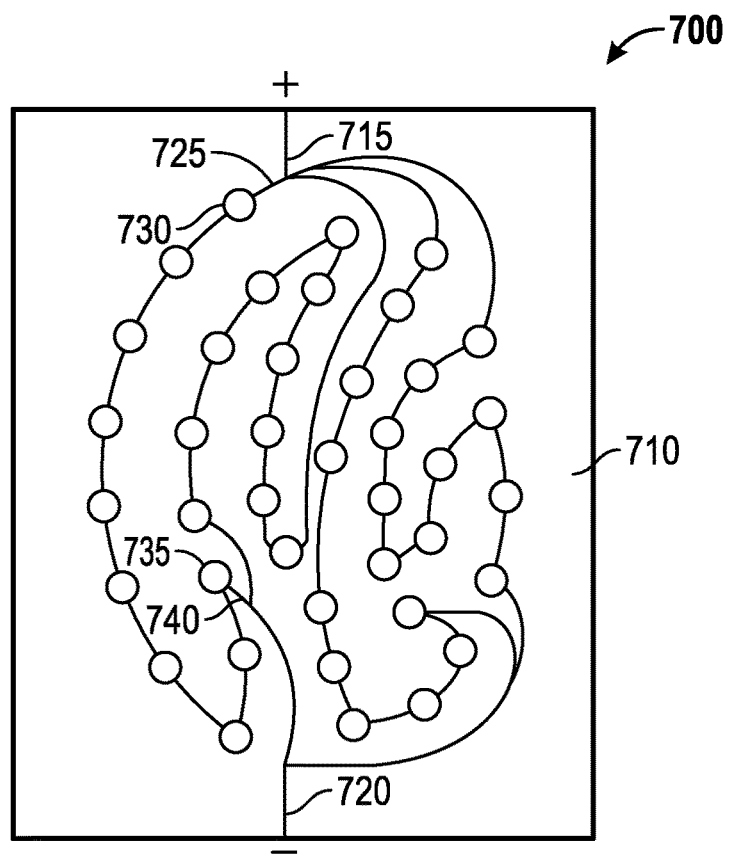
FIG. 7 is block schematic representation of wired sockets for a matrix of modules according to an example embodiment.

FIG. 7 is a block diagram schematic representation of a connector board for a high intensity light emitting diode array shown generally at 700. Openings in the board for the cooling structures are not shown. In one embodiment, a board 710 is provided with a positive connector 715 and a negative connector 720 for connection to a power source and driver, not shown. Positive connector 715 is electrically coupled via a connector 725 to a first socket 430. Given one example supply of 24 volts across connectors 715 and 720, ten sockets may be serially electrically coupled, ending with socket 735, which in turn, is coupled via connector 740 to negative connector 720. These connections, together with intermediate serial connections to eight other sockets provides a voltage drop of 2.4 volts DC for each light emitting diode plugged into the socket. This ensures that each light emitting diode will receive the proper voltage for proper operation. It should be noted that different light emitting diodes may have different voltage drops, and many more light emitting diodes may be coupled in series in further embodiments. Sixty or more such light emitting diodes may be coupled in series in some embodiments, with the voltage supply being adjusted according to the expected voltage drop across each diode.

If a different supply level is provided, and/or different light emitting diodes are used with different voltage drops, it is a simple matter to divide the supply by the voltage drop to determine how many sockets should be connected serially. The board may then be reconfigured consistent with the number of sockets needed. As shown in FIG. 7, there are four such sets of serially connected sockets, each being coupled between the positive and negative connectors 715 and 720. Many other different configurations are possible.

In still further embodiments, adaptive power supplies may be used, and the number of modules in series may be varied with the supply adapting to the proper output required to drive the modules. All sockets may be active with such drivers and modules plugged in as desired. In some embodiments, modules may be removed or added in series if needed to be compatible with the supply and driver circuitry. All the sockets may be wired in series in one embodiment. Plugs to short circuit open sockets may be used to maintain the series connection, or suitable bypass circuitry may be used to maintain a series connection if modules in sockets have malfunctioned, or sockets are not used in some lighting applications.

In one embodiment, the current sockets are arranged in an oval shape, but many other shapes may be easily used. The board 710 may be suitably shaped to conform to the sockets to provide a shape suitable for aesthetic design purposes. Similarly, the matrix 405 as shown in FIG. 4 may also take many different shapes, from rectangular or circular as shown to just about any shape desired, such as "u" shaped or kidney bean shaped to name a few. Further, elongated shapes of one or more rows of series coupled sockets may be provided.

The matrix 405 and board 430 in some embodiments may be made of any weather resistant metal such as aluminum, copper, or other material suitable for dissipating heat. In one embodiment, the electrical sockets are in a uniformly disbursed triangular matrix in relation to each other and may be part of a cast matrix 405.

In one embodiment, the electrical sockets 450 may be designed to accommodate a removable and replaceable light emitting diode module with different connection types including, but not limited to, screw-in or Edison type connections, a bayonet-type connection, and snap-in or friction connection as illustrated at 800 in FIG. 8.

In FIG. 8, a module 805 is secured via male conducting pins 810, 815 into mating connectors 820, 825 in a board 830. The conducting pins and mating connectors provide for a snap-in or friction connection that holds the module 805 securely within a socket 835. In one embodiment, the mating connectors 820 and 825 may be provided with guides 826 that ensure that the pins are properly inserted and guided into the female mating connectors 820, 825, which may be made of brass in one embodiment and be spring loaded from the sides to retentively engage the pins 810, 815. The female connectors may extend partly above the board, or within the board in various embodiments. When within the board, the board essentially has a larger opening than the diameter of the pins, and narrows to the point of the snap-in or friction connection portion of the matting connectors.

In one embodiment, a sealing member such as a ring, disk or washer 840 is positioned between the module 805 and a surface of the socket 835. The sealing member 840 is compressed when the module 805 is fully secured by the pins and mating connectors to provide a watertight seal and protect the electrical connections from elements which might degrade the electrical contact formed by such connections. In various embodiments, the sealing member may be formed of rubber, latex, Teflon, silicon rubber or like compressible material. To provide for larger tolerances with respect to the thickness of the board 830 and the distance of the connectors 820, 825 from the module when seated in the socket, the compressible sealing member may be formed with a hollow center in some embodiments. In further embodiments, the sealing member operates to provide a seal over a wide depth of compression.

In a further embodiment, plugs may be formed in the same shape as module 805, having pins that mate with the mating connectors 820, 825 to provide a seal around sockets that are not used for operational modules. The pins of such plugs may be electrically isolated from each other to ensure that no short circuits occur, or may provide a short circuit to maintain a series connection in a pre-wired string of sockets. Such plugs ensure integrity of all electrical connections in the board when properly used in all sockets not containing modules 805.

The ability to easily remove and replace modules in a sealing manner facilitates maintenance and repair of high intensity large volume matrix lighting solutions. Each individual light emitting diode module may be removed from an individual socket within the matrix. Because the individual light emitting diode modules are individually replaceable, if one module fails there is no need to replace an entire bundle or group of electrical sockets or modules. Simple removal and replacement of the failed module may be quickly performed. Furthermore, light emitting diode modules emitting different colors may be rearranged within the matrix to produce different color arrangements without replacement of the entire bundle of electrical sockets or modules.

Module 805 also illustrates a lens 850 coupled to the light emitting diode within module 805 and providing a protective seal. The lens 850 may be placed on and adhered to a filling material surrounding the actual light emitting diode. As the filling material solidifies, the lens may be securely fastened to the filling material. Many different types and shapes of lenses may be used. For large area high intensity lighting applications, the lens may be shaped to provide directional lighting, or a widely dispersed beam of light such that when all the modules in an array are properly oriented, a desired pattern of light is provided to light a large area, such as a parking lots, parking ramps, highways, streets, stores, warehouses, gas station canopies. Similarly, different lenses may be used for many different applications, such as for forming spotlights, narrow beams from each module may be desired.

Module 805 may also be provided with guides 845, which along with mating guides in a socket, ensure that the module is inserted into the socket in a desired orientation. In one embodiment, the guides 845 may be ridges extending outward from the module and mating with grooves in the module to provide a guide. In further embodiments, the grooves may be on the module with mating ridges on the socket. Many different shapes and combinations of grooves and ridges may be provided in various embodiments.

In yet a further embodiment, board 830 may be formed with a filling material 5860, and a further board 865. Such a combination provides a seal for the conductors on the board and protects them from the elements.

FIG. 9 is a further embodiment 900 of a screw in type of connector, commonly referred to as an Edison connector. A sealing member is also provided. In this embodiment, a simple cylinder may be used as the socket, with the top portion of the module with the sealing member simply compressed against the top of the socket when the module is fully engaged in a retentive relationship with the socket.

FIG. 10 is a further embodiment 1000 of a bayonet type connector, also having a sealing member that is similarly compressed.

Figure 11:
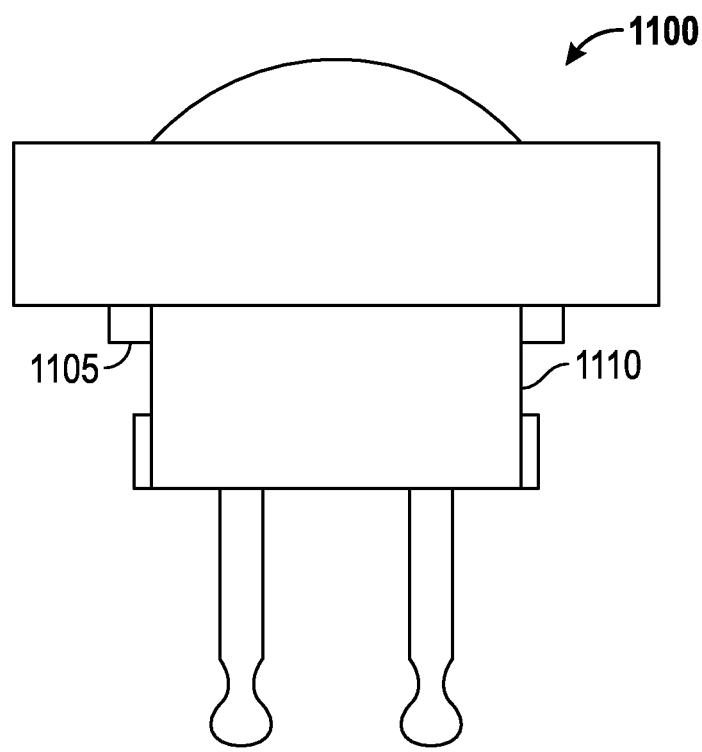
FIG. 11 is a block cross sectional view of a module having a different connection mechanism to provide a sealed connection with a socket according to an example embodiment.

FIG. 11 is an alternative embodiment 1100 to the module 805 of FIG. 8, where the sealing member 1105 is positioned over the base 1110 of module 1100. The pins are also similar in that they provide friction fit with connectors on a board.

Figure 12:
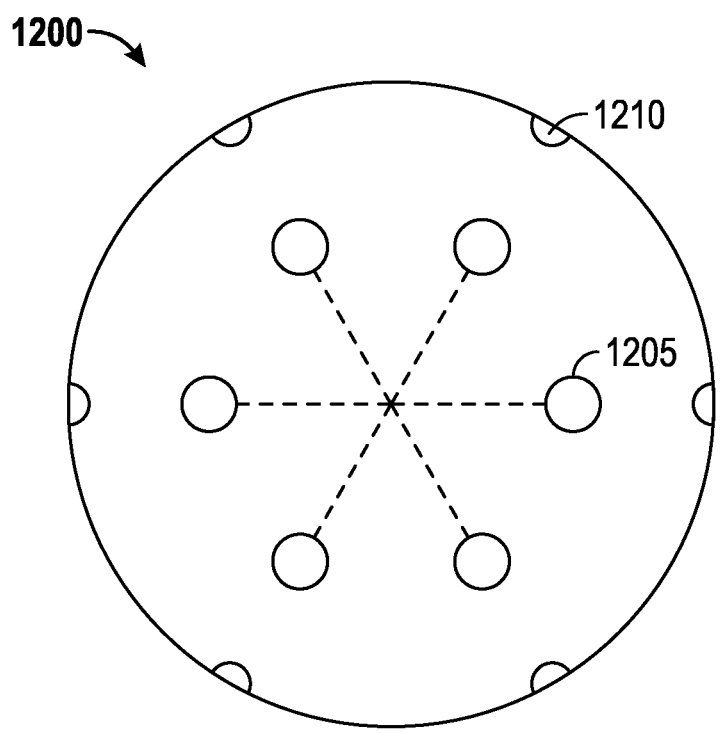
FIG. 12 is a top view of connectors on a board for providing electrical connection to a module according to an example embodiment.

FIG. 12 is a block diagram schematic view of the bottom of a socket 1200, into which pins of the modules may be inserted. Six openings 1205 are illustrated, representative of connectors for three differently oriented sets of pins. Also shown are grooves 1210 for providing a guide so modules are properly inserted. In one embodiment, the board may have three or more different sets of wiring to provide different circuits for different types of LED modules, such as different color LEDs. The different circuits may then be used to control the different color LEDs independently and in a desired manner, and as further discussed below to provide different color and intensity light. The differently oriented sets of pins along with grooves in one embodiment are formed to ensure that a light of one color may only be plugged into a socket in a desired manner to connect to the desired circuit. In further embodiments, signals to control of lights may be multiplexed onto one or more control lines to provide separate circuits for desired control of lights without having to plug them into the socket in different alignments. Still further, sockets may be prewired for a certain type of LED module. In still further embodiments, sockets may be twisted or otherwise oriented within a socket to make contact to a desired circuit.

In one embodiment, a circuit board may have 240 available sockets for modules, to allow flexibility in positioning modules. In some embodiments, different types of modules, such as different color modules may be interspersed throughout the board. In one example, 90 white light modules, and 30 yellow light modules may be properly inserted into sockets and independently controllable, either by separate circuits, or by predetermined wiring. Many other different combinations and total numbers of sockets per circuit board may be used in further embodiments, including boards that support 60 to 90 sockets, 90 to 120 sockets, and 120-160 sockets for example.

Figure 13:
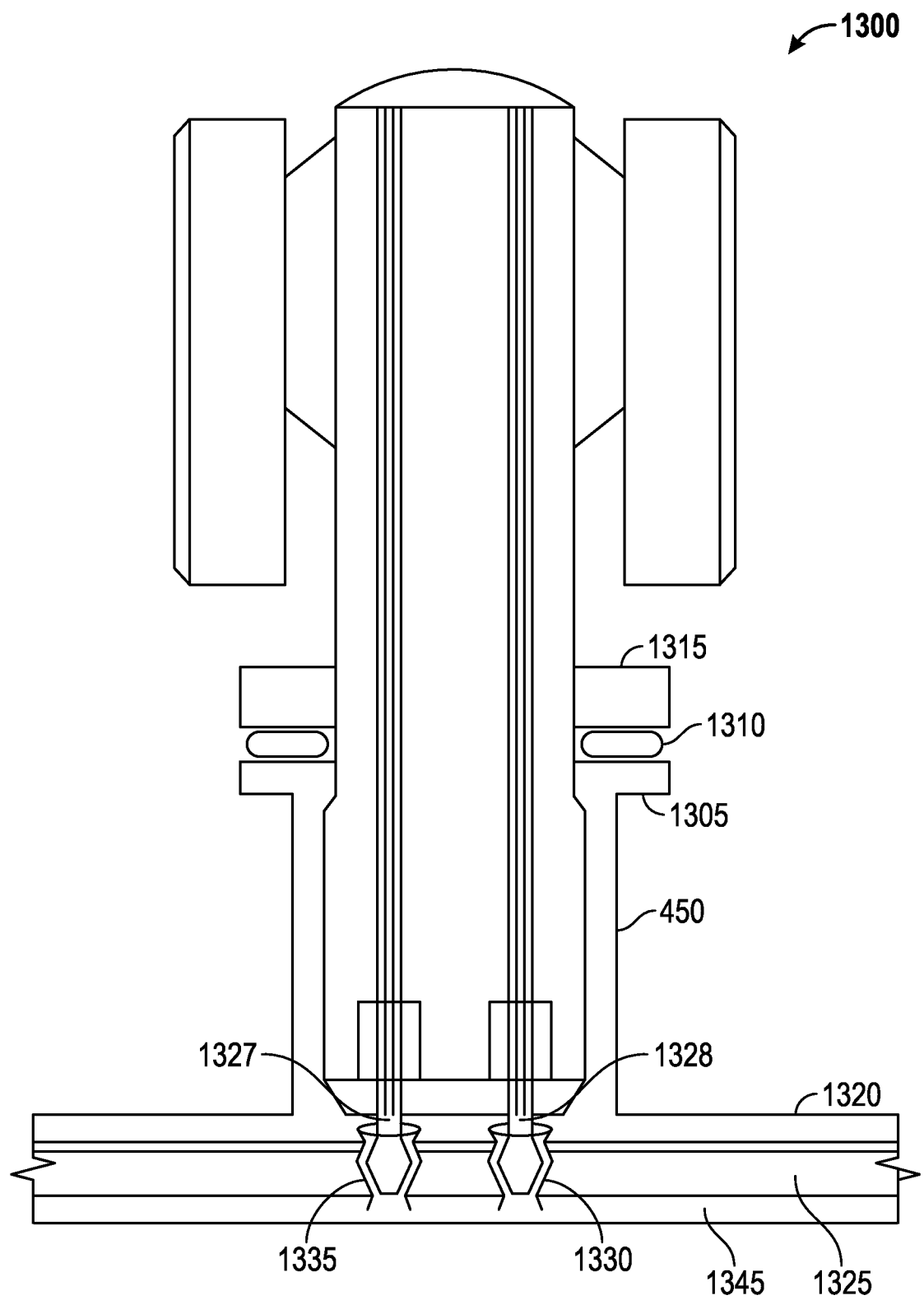
FIG. 13 is a block cross section view of an alternative module supported in a socket according to an example embodiment.

FIG. 13 is an alternative embodiment of a module 1300 plugged into a socket 450. In this embodiment, socket 450 has a flange 1305 at a module-receiving end that operates to provide a surface for compression of sealing material 1310 between flange 1305 and a ring 1315 formed on a base of module 1300. Socket 450 also has a second flange 1320 formed on a second end that abuts board 1325. In this embodiment, pins 1327, 1328 extend a short distance from a body 1330 of module 1300 to mate with female connectors 1335 and 1330. The female connectors 1335, 1330 may extend beyond the circuit board into a compressible adhesive material 1345 in some embodiments.

Figure 14:
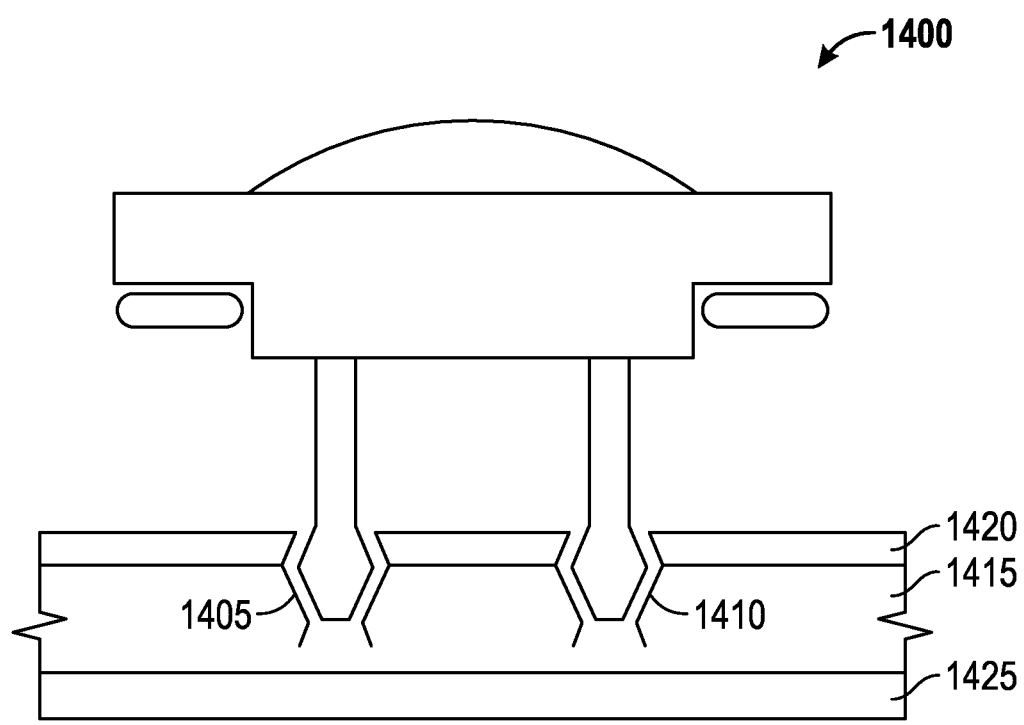
FIG. 14 is a block cross section view of an alternative module for plugging into a board according to an example embodiment.

FIG. 14 shows an alternative module 1400, wherein the female connectors 1405 and 1410 extend significantly into a compliant adhesive material 1415 between boards 1420 and 1425. The material 1415 provides additional spring force for maintaining retentive force on the pins via female connectors 1405 and 1410. In one embodiment, the material 1415 may be a liquid rubber, latex, or silicon type material that is pliable and provides good adhesion over the boards.

Figure 15:
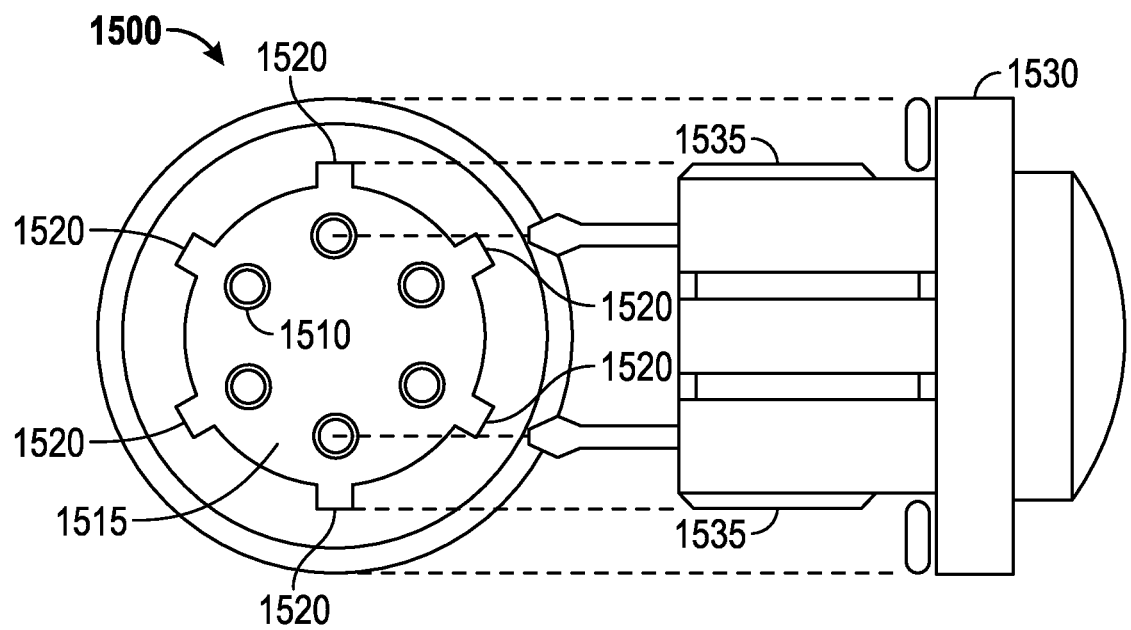
FIG. 15 is a top view of a connector and side view of a module for plugging into the connector according to a further example embodiment.

FIG. 15 is a top view of multiple sets of female connectors 1510 on a board 1515 for mating with pins of a module 1530. Grooves 1520 are also provided in the sides of the socket corresponding to the connectors to provide for guiding the module 1530 having a pair of mating ridges 1535. In one embodiment, the module may be coupled to one of three different sets of connectors by rotating the module and inserting it. The positions in which the module may be inserted may be referred to as A, B and C in one embodiment. Position A may correspond to wiring on the board such that 80 modules may be inserted into sockets to provide lighting for an application requiring that amount of light. Position B may accommodate 120 modules, while position C may accommodate 160 modules. The particular numbers of modules may be varied considerably in different embodiments. In one embodiment, two grooves 1520 may be provided, and rotated to different positions to ensure that the module is properly inserted depending on the application desired. Templates may also be used for each different configuration to help a user insert modules into the proper sockets. After use of the template, the remaining open sockets may have plugs inserted to ensure that the lighting fixture is properly sealed.

Figure 16:
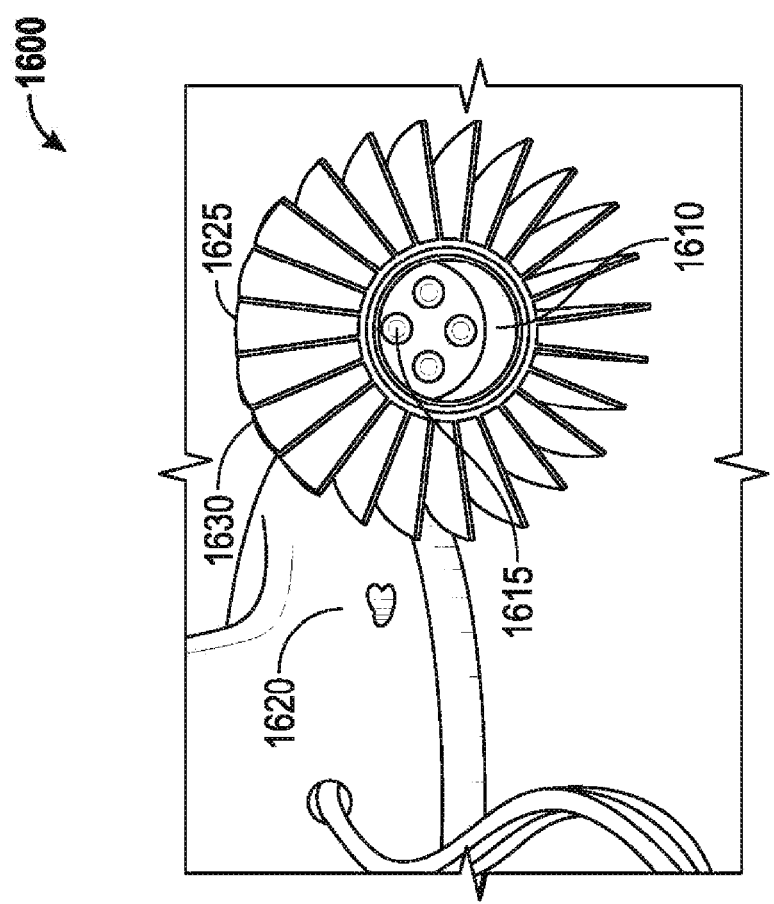
FIG. 16 is a perspective view of a light emitting diode based light bulb having light reflective surfaces according to an example embodiment.

FIG. 16 is a perspective view of a light emitting diode based light bulb 1600 having light reflective surfaces according to an example embodiment. A central tube 1610 is illustrated with a light emitting diode package 1615 positioned a selected depth into the tube 1610. The depth may be selected to enable insertion and retention of one of many different rods to disperse light in different patterns for different applications. The depth may further be selected to facilitate heat transfer by a heat sink, which includes multiple light reflective fins 1620.

In one embodiment, both sides of the fins 1620 are reflective to light generated by the light emitting diode. The inside of tube 1610 is also reflective in one embodiment to facilitate reflection of light, and to minimize absorption of heat from the light. Still further, the outside of tube 1610 may also be reflective, as is a top surface 1625 of an electronics module 1630. Making one or more surfaces proximate the light emitting diode reflective of light generated by the light emitting diode can provide the benefit of further light dispersal and less heat being absorbed by the light bulb 1600, as less of the generated light is absorbed by non-reflective surfaces. In still further embodiments, a PCB board on which the light emitting diodes are supported may also be reflective.

In one embodiment, the fins 1620 may be formed by folding a material that is reflective on at least one side and crimp fitting the folded material between slots formed in the outside of the tube 1610. In other embodiments, a fin may be formed that is reflective on both sides, and need not be folded. While 24 fins are shown, fewer or more fins may be used in further embodiments. The number of fins may vary based on aesthetic design desires, reflective properties, and thermal dispersion properties.

As indicated in one example embodiment, the fins extend further from the top of the tube, and then taper down to extend a similar radius out from the tube as the radius of the electronics module, creating a lean shape, similar to that of a common incandescent light bulb, albeit slight wider than the normal connector to a standard Edison socket. The width of the electronics module may be larger than a standard Edison socket in order to accommodate circuitry utilized to drive the led package. In some embodiments, larger capacitors may be used that take up space. Some electronic elements may extend into the tube and even into the male Edison connector portion of the light bulb.

Figure 17:
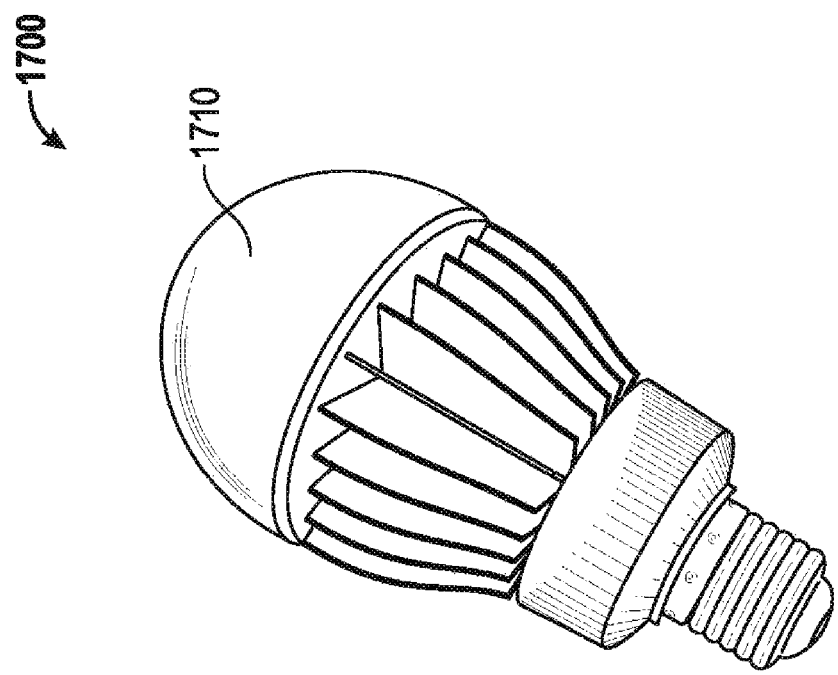
FIG. 17 is a perspective view of a light emitting diode based light bulb having light reflective surfaces and a cloudy dome cover according to an example embodiment.

FIG. 17 is a perspective view of a light emitting diode based light bulb 1700 having light reflective surfaces and a cloudy dome cover 1710 according to an example embodiment. The light bulb 1700 is similar to bulb 1600 with the addition of the dome cover 1710 that meets the edges of the fins at the top of the tube in one embodiment forming a smooth shape and creating a soft dispersed light. The dome may be formed of different materials, such as glass or plastic, and may be transparent or cloudy relative to visible light. Not shown is a rod shaped lens extending from the light emitting diode through the top of the tube and into the dome cover 1710. The likely type of rod will have a divot in the top to disperse light inside the dome cover and provide an amount of light very similar to that of a standard soft 100 watt incandescent bulb while only consuming 13 watts of electricity or less depending on efficiency of the LED and electronics. In some embodiments, over 80 lumens per watt are generated by the light emitting diode package. Also illustrated in FIG. 17 are a standard Edison connector coupled to the electronics package. In one embodiment, the tube provides a passage between the electronics package and the light emitting diode package for appropriate wiring and supply of electricity to the light emitting diode package.

Figure 18:
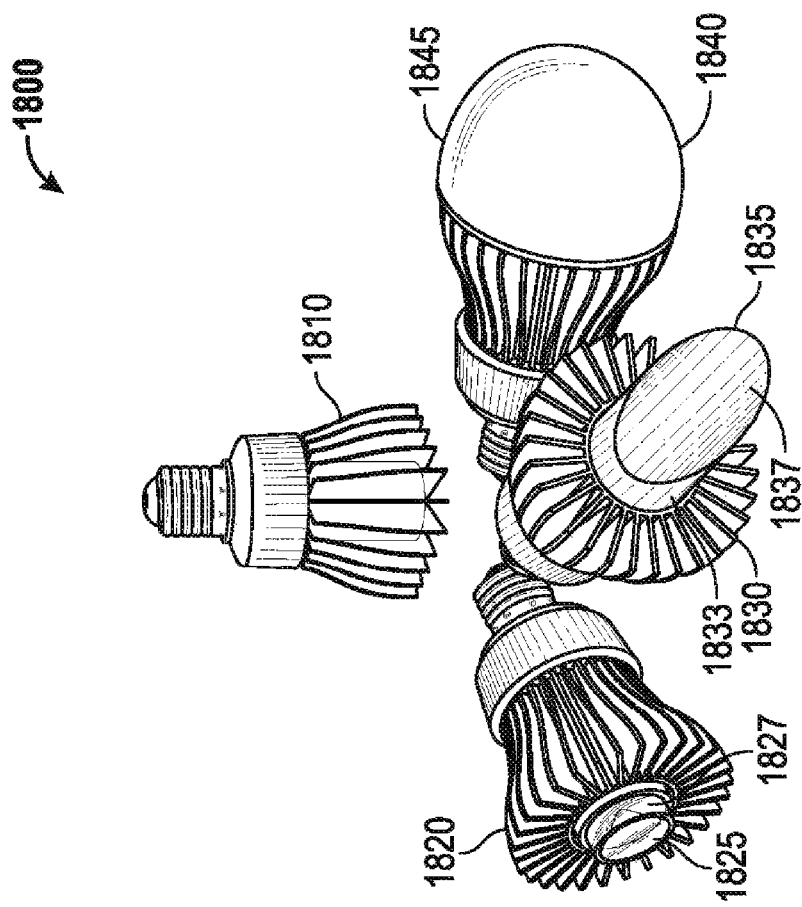
FIG. 18 is a perspective view of multiple light emitting diode based light bulbs having light reflective surfaces and various lenses for different applications according to an example embodiment.

FIG. 18 is a perspective view of multiple light emitting diode based light bulbs having light reflective surfaces and various lenses for different applications according to an example embodiment. Bulb 1810 is the same as bulb 1600, just shown top side down on a flat surface. It illustrates how the fins are assembled into the tube and have top edges that may be co-planar with the top of the tube The edges may be lower than or higher than the top of the tube in further embodiments.

Bulb 1820 is shown with a short lens 1825 that may have a flat top surface for emitting light in a pattern similar to that of a spot light or flood light. The lens 1825 includes a reflective collar 1827 extending from the top of the tube a distance along a length of the lens to facilitate projection of the light out the top of the lens 1825. In various embodiments, the side of the collar adjacent the lens is reflective to light emitted from the light emitting diode. The outside of the collar may also be reflective. The collar may extend the full length of the lens in some embodiments, or only a portion of the length of the lens depending on the dispersal pattern of light that is desired.

Bulb 1830 is shown with a similar collar 1833 and a lens 1835 with a tapered edge indicated at 1837. The tapered edge 1837 provides for more light dispersion directed out from the flat surface of the lens created by the taper than dispersed from other sides of the lens.

Bulb 1840 is shown with a clouded plastic dome shaped cover 1845 that creates a software light bulb like dispersion from a lens inside the cover. As previously indicated, the bulb 1840 appearance is more like that of a standard incandescent soft light bulb except for a wider base where it contacts the Edison style connector portion of the bulb.

Many different types of lenses may be used, with the base becoming a standard part that can be used for many different types of light bulbs suitable for different applications, such as in a lamp shade, a street light using an array of light bulbs, a trouble light, spot light, flood light, etc. It should also be noted that in some embodiments none or only some of the components are reflective. The rod lens can formed of plastic, glass, or other transparent or semi-transparent material.

In further embodiments, the rod cross section may take many different shapes, such as round, star shaped, square shaped, triangular shaped, etc. It may also be multi-faceted to produce different types of effects. Where a divot is used in the end of the rod, the divot may be cone shaped or even multifaceted in some embodiments to produce a cut gemstone-like appearance.

Figure 19:
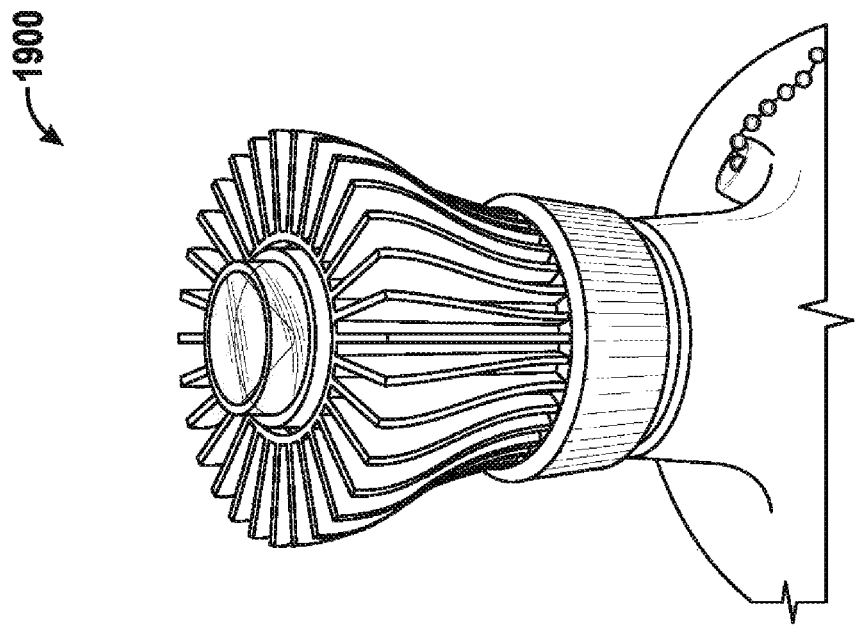
FIG. 19 is a perspective view of a light emitting diode based light bulb having reflective surfaces and shown secured in an electrifiable socket according to an example embodiment.

FIG. 19 is a perspective view of a light emitting diode based light bulb 1900 having reflective surfaces and shown secured in an electrifiable socket according to an example embodiment. A short lens with collar is also illustrated. In the background is a bowl full of different lenses that may be used to create different lighting effects.

Figure 20:
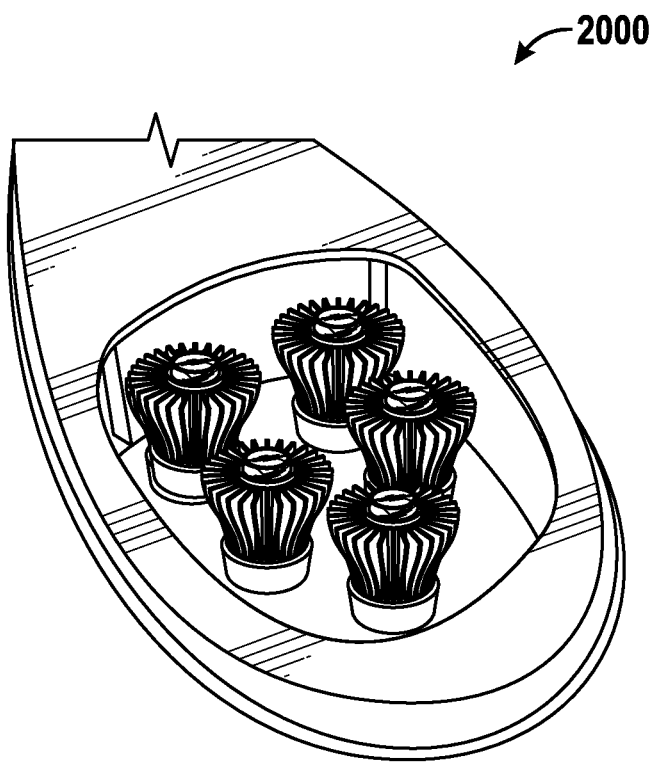
FIG. 20 is a perspective view of a street light shell having multiple light emitting diode based light bulbs secured in multiple electrifiable sockets according to an example embodiment.

FIG. 20 is a perspective view of a street light shell 2000 having multiple light emitting diode based light bulbs secured in multiple electrifiable sockets according to an example embodiment. A short lens with collar is also illustrated for each bulb, providing multiple flood light elements that create a downward directed light when the shell is positioned facing downward, facing the ground. The shell is suitable for lighting parking lots, streets, intersections, playgrounds, and other outdoor and even indoor areas, while consuming significantly less energy and faster turn on times than current light sources utilized for high intensity lighting applications.

Figure 21:
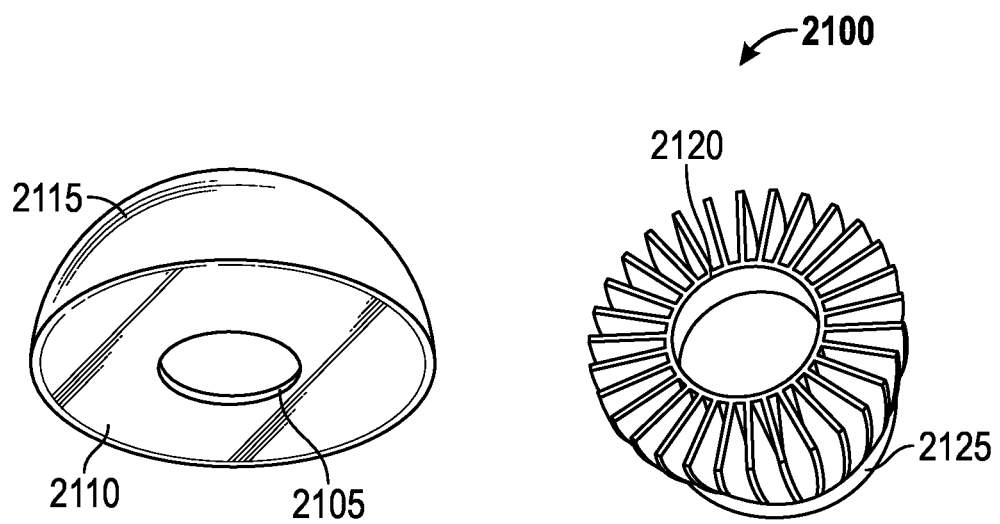
FIG. 21 is a perspective view of a top and bottom half of a light emitting diode based light bulb according to an example of embodiments.

FIG. 21 is a perspective disassembled view of a further example light emitting diode based light bulb 2100. A top portion of the light bulb 2100 consists of a rod-like lens 2105 coupled through a transparent plate 2110. In one embodiment, the plate 2110 is formed of plastic and has an opening that is the size of the diameter of the lens 2105 such that the lens fits retentively into the plate and extends away from both sides of the plate. In further embodiments, the lens and plate can be a single piece formed by a process such as injection molding. The circumference of the plate is about the size of standard incandescent 100 watt bulb in some embodiments, and is coupled to a cloudy dome structure 2115. The rod extends from the plate into the dome a selected distance, and may end in a divot as described above to disperse light about an angle of 360 degrees. The divot may be adjacent the top of the dome, or a selected distance between the plate and the top of the dome.

As indicated, a portion of the rod extends out the other side of the plate to couple the plate and dome to a tube 2120 portion of the light bulb 2100 that contains one or more light emitting diodes recessed into the tube. The rod 2105, when assembled, extends into the tube in a manner that securely retains the top portion of the light bulb 2100. This may be accomplished via a friction fit, a snap fit where a portion of the rod may have a recession or protuberance that makes with a corresponding protuberance or recession in the tube, or even via matting threaded portions on the rod and tube to hold the rod in the tube a selected distance from the light emitting diodes. The distance may be obtained by positioning of the snap fit features, threads, one or more ledges within the tube or on the lens, or by any other means. The tube is also coupled to heat sink fins as illustrated, and to an electronics base 2125 and Edison connector as shown in previous figures.

Figure 22:
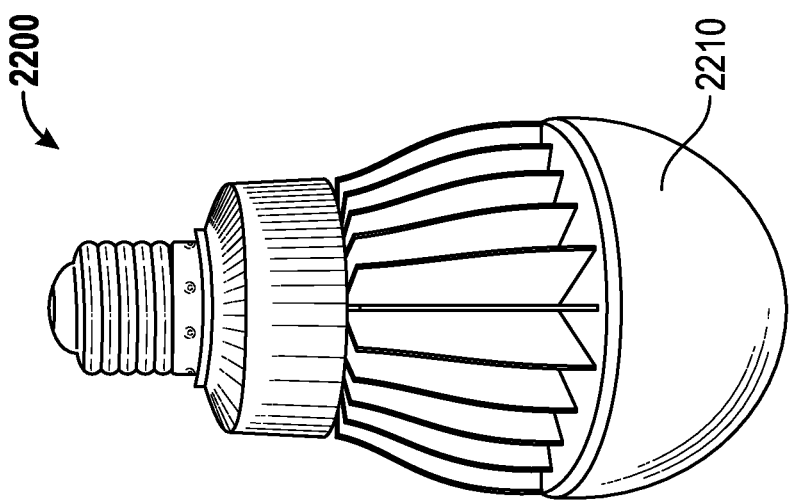
FIG. 22 is a perspective view of an assembled light emitting diode based light bulb according to an example embodiment.

FIG. 22 is a perspective view of a further light bulb 2200. Light bulb 2200 includes a dome 2210 that is shaped a cylinder for a first portion extending from the fins, and ends in an arcuate dome shape. Much as the rod or lens may be replaced to provide different effects, the dome may also be varied from clear to cloudy, providing even more manufacturing flexibility to produce bulbs for different purposes.

Figure 23:
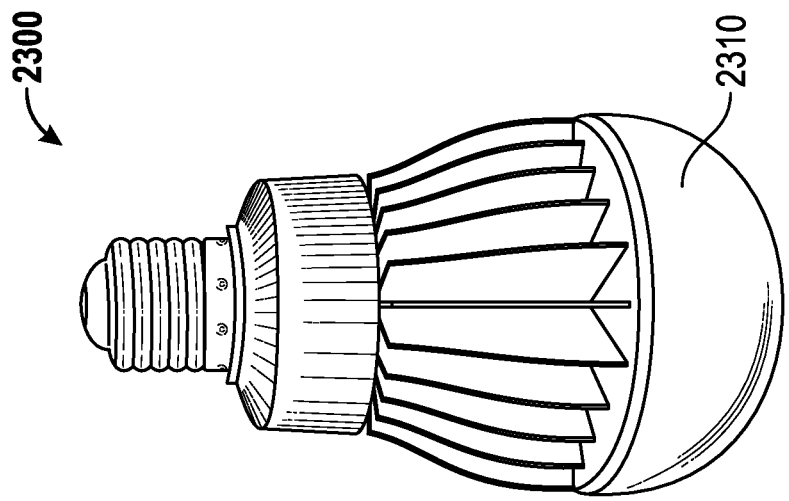
FIG. 23 is a perspective view of a further embodiment of an assembled light emitting diode based light bulb according to an example embodiment.

FIG. 23 is a perspective view of a further light bulb 2300. Light bulb 2300 includes a dome 2310 that has an arcuate dome shape, lacking the cylindrical portion of dome 2210. Many different styles of domes may be used, and permit the design of a light emitting diode based light bulb that produces at least an equivalent amount of light when compared to various 100 watt incandescent bulbs or other bulbs. The dome shapes also provide the ability to imitate the light dispersal characteristics of different bulbs, allowing substitution in many different types of fixtures while maintaining the intended lighting aesthetics of the fixtures. In other words, the center of light emission and amount of light emitted may be varied utilizing different length and type rods and different dome shapes, to obtain light emitting characteristics similar to those for which a fixture may have been designed. Additionally, a standard base may be utilized for many different light bulb designs.

Figure 24:
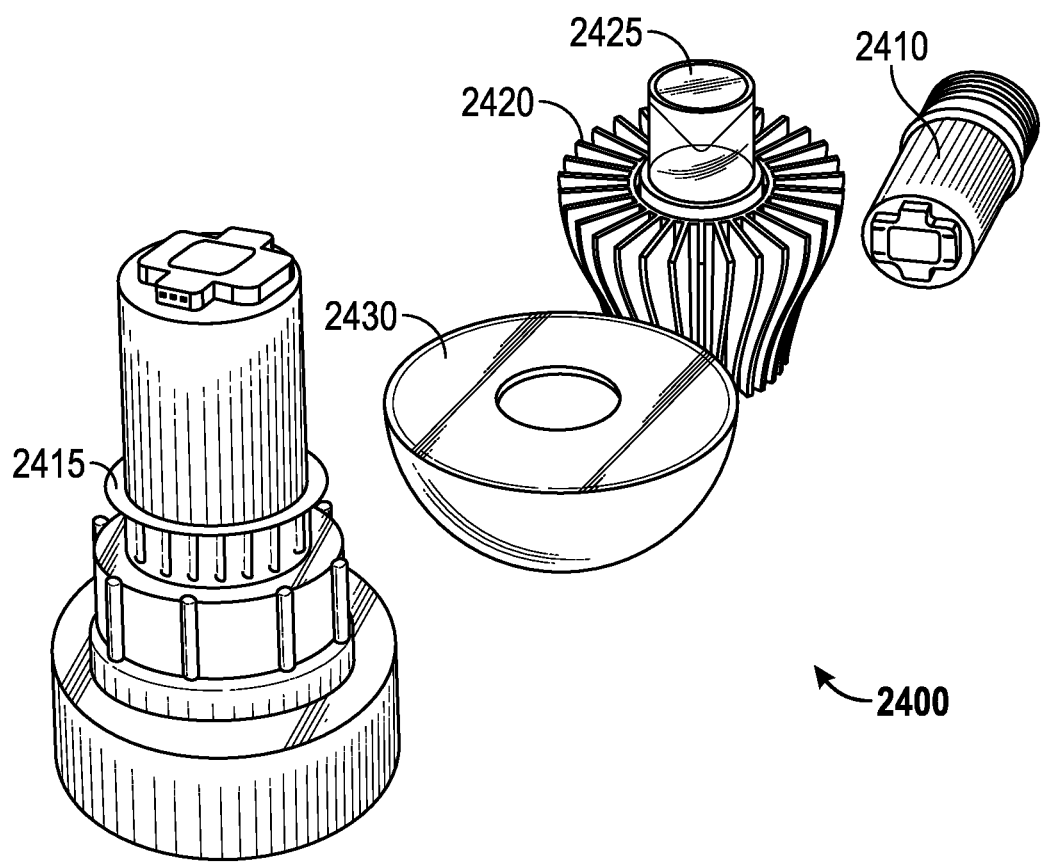
FIG. 24 is an exploded perspective view of an alternative light emitting diode based light bulb according to an example embodiment.

FIG. 24 is an exploded perspective view of an alternative light emitting diode based light bulb. A central tube 2410 is illustrated with a light emitting diode package positioned inside the central tube, which is substantially cylindrical in shape of a tube. The light emitting diode package includes electronics positioned within the tube, and a light emitting diode positioned at one end of the tube, and an Edison type socket positioned at the other end of the tube. A lip 2415 positioned near the Edison type socket may help align a heat sink that fits around the tube.

In one embodiment, the light emitting portion of the light emitting diode package may extend to or beyond the end of the tube in order to allow for broad dispersal of emitted light. The heat sink 2420, when assembled with the tube may extend beyond the light emitting diode, creating a cylindrical opening in which the lens 2425 may be supported and optionally fixed adjacent the light emitting diode in a secure manner, such as by use of silicon or other suitable adhesive. The depth of the cylindrical opening may be selected to enable insertion and retention of one of many different rods to disperse light in different patterns for different applications. The depth may further be selected to facilitate heat transfer by the heat sink, which includes multiple fins.

In one embodiment, the heat sink 2420, including the fins may be a single part of clear glass, plastic, or Plexiglas to increase the number of lumens per watt emitted to ambient from the light bulb. The clear heat sink embodiment may allow a light having an 8-13 watt LED to emit light equivalent to a 100 watt incandescent bulb. The transparent fins also reflect light from the light emitting diode, further enhancing the number of lumen per watt. Making one or more surfaces proximate the light emitting diode reflective of light generated by the light emitting diode can provide the benefit of further light dispersal and less heat being absorbed by the light bulb, as less of the generated light is absorbed by non-reflective or opaque surfaces. In still further embodiments, a PCB board on which the light emitting diodes are supported may be reflective.

In various embodiments, the number of fins may vary based on aesthetic design desires, reflective properties, and thermal dispersion properties.

As indicated in one example embodiment, the fins extend further from the top of the tube, and then taper down to extend a similar radius out from the tube as the radius of the electronics module, creating a lean shape, similar to that of a common incandescent light bulb, albeit slight wider than the normal connector to a standard Edison socket. The width of the electronics module in one embodiment is the same as or less than a standard Edison socket in order to accommodate circuitry utilized to drive the led package. In some embodiments, the circuitry includes sensors to sense temperature, and circuitry to reduce a duty cycle to ensure that the electronics are not subjected to excess heat that may decrease the mean time between failure of the electronics, allowing the electronics to function for the same amount of time as the projected lifetime of the light emitting diode. While this may result in periods of fewer lumens during times of high ambient temperatures, the effect should be well worth the tradeoff of a longer light bulb life. In addition, the feature may also aid utility companies in reducing peak demand during periods of high ambient temperatures. Some electronic elements may extend into the tube and even into the male Edison connector portion of the light bulb.

In one embodiment, a dome cover 2430 may be adapted to snap fit to and over the tops of the fins of the heat sink. In this embodiment, the dome cover 2430 is not supported by the lens, but rather by the fins, with the lens 2425 supported in the cavity formed by the combination of the central tube and heat sink. This results in a very easy to assemble LED based light bulb, with various power ranges, currently from 8 or less to 15 or more watts, producing lumens equivalent to 100 watt to 250 watt incandescent light bulbs. In still further embodiments, the dome 2430 may be shaped to connect to the fins or central tube at or near the central tube. In one embodiment, the dome 2430 then extends out from at or near the central tube to the exterior of the fins prior to extending upwards, such that the light bulb still has a shape similar to a standard 100 watt incandescent bulb, or other bulb, such as a flood light shape, candelabra shape, or other shape.

Figure 25:
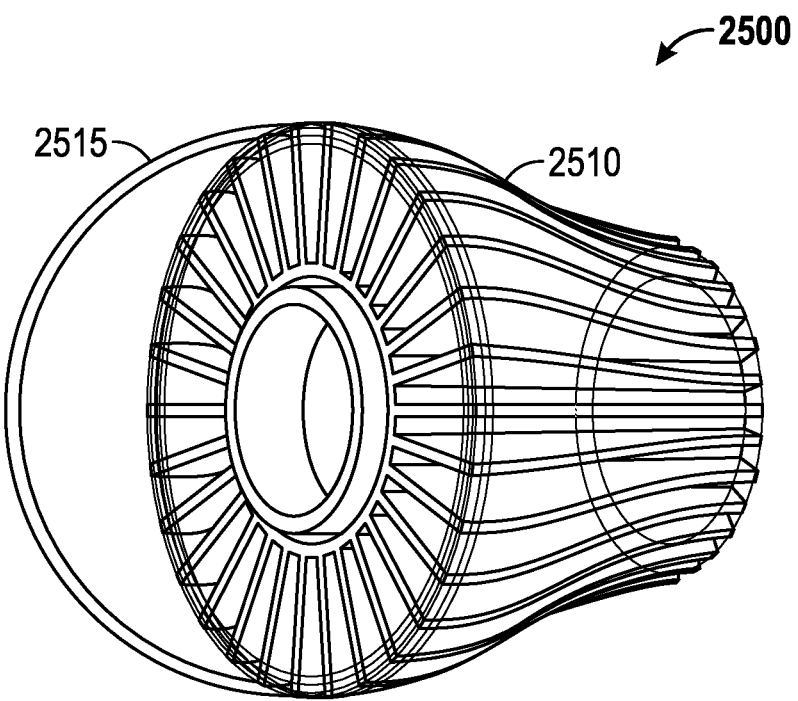
FIG. 25 is a wireframe view of an alternative light emitting diode based light bulb according to an example embodiment.

FIG. 25 is a wireframe view of an alternative light emitting diode based light bulb according to an example embodiment. In one embodiment, the heat sink and fins 2510 may be formed from a single body. The heat dissipating fins may extend radially from the heat sink core, drawing heat away from the light emitting diode, and acting as a heat sink to prevent damage to the light emitting diode or the surrounding components. In various embodiments, the number of fins may vary based on aesthetic design desires, reflective properties, and thermal dispersion properties. As indicated in one example embodiment, the fins extend further from the top of the tube, and then taper down to extend a similar radius out from the tube as the radius of the electronics module, creating a lean shape, similar to that of a common incandescent light bulb, albeit slight wider than the normal connector to a standard Edison socket. In one embodiment, a dome cover 2515 may be adapted to snap fit to and over the tops of the fins of the heat sink. In one embodiment, the heat sink and fins may be formed of glass to provide strength, heat conduction, and low thermal expansion. The glass may be the same glass used to make soda bottles, and equipment for making soda bottles may be modified simply to make a one piece heat sink that includes the fins.

Figure 26:
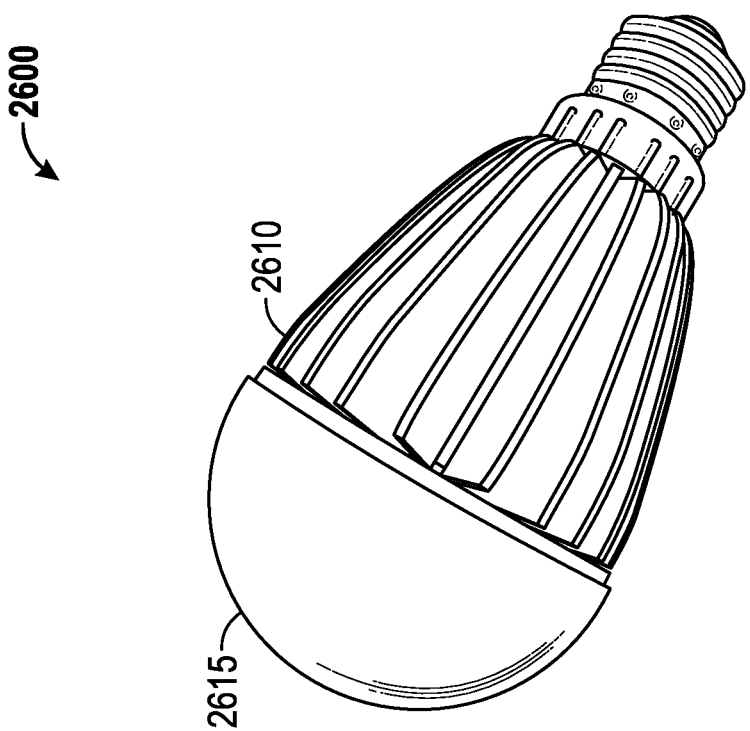
FIG. 26 is a perspective view of a further embodiment of an assembled light emitting diode based light bulb according to an example embodiment.

FIG. 26 is a perspective view of a further embodiment of an assembled light emitting diode based light bulb according to an example embodiment. In one embodiment, the heat sink and fins 2610 may be formed of glass to provide strength, heat conduction, and low thermal expansion. In an embodiment, the heat sink core and heat sink fins 2610 may be formed from a single body. In another embodiment, the heat sink fins 2610 may be fixedly attached to the heat sink core.

Using glass to form the heat sink, fins 2610, and dome 2615 may increase the number of lumens per watt emitted to ambient from the light bulb. The transparent glass fins 2610 also reflect light from the light emitting diode, further enhancing the number of lumen per watt. Making one or more glass surfaces proximate the light emitting diode reflective of light generated by the light emitting diode can provide the benefit of further light dispersal and less heat being absorbed by the light bulb.

Figure 27:
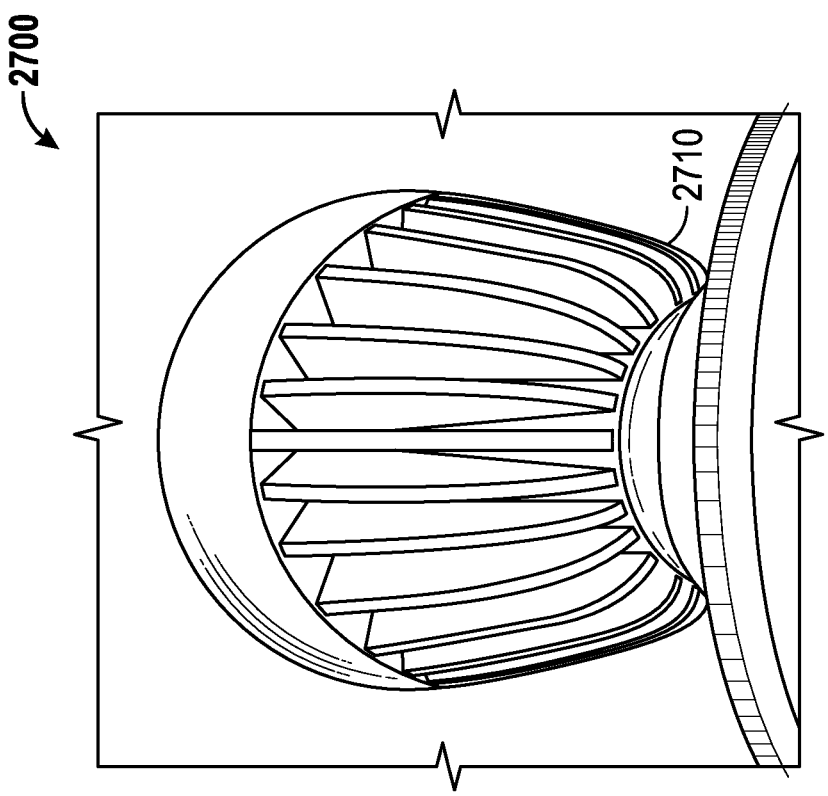
FIG. 27 is a perspective view of a further embodiment of an assembled light emitting diode based light bulb according to an example embodiment.

FIG. 27 is a perspective view of a further embodiment of an assembled light emitting diode based light bulb according to an example embodiment. In one embodiment, the heat sink and fins 2710 may be formed of glass. The planar glass surfaces between the fins reflect light from the light emitting diode, further enhancing the number of lumen per watt. In another embodiment, the heat sink fin edges may be rounded to improve light dispersal.

Figure 28:
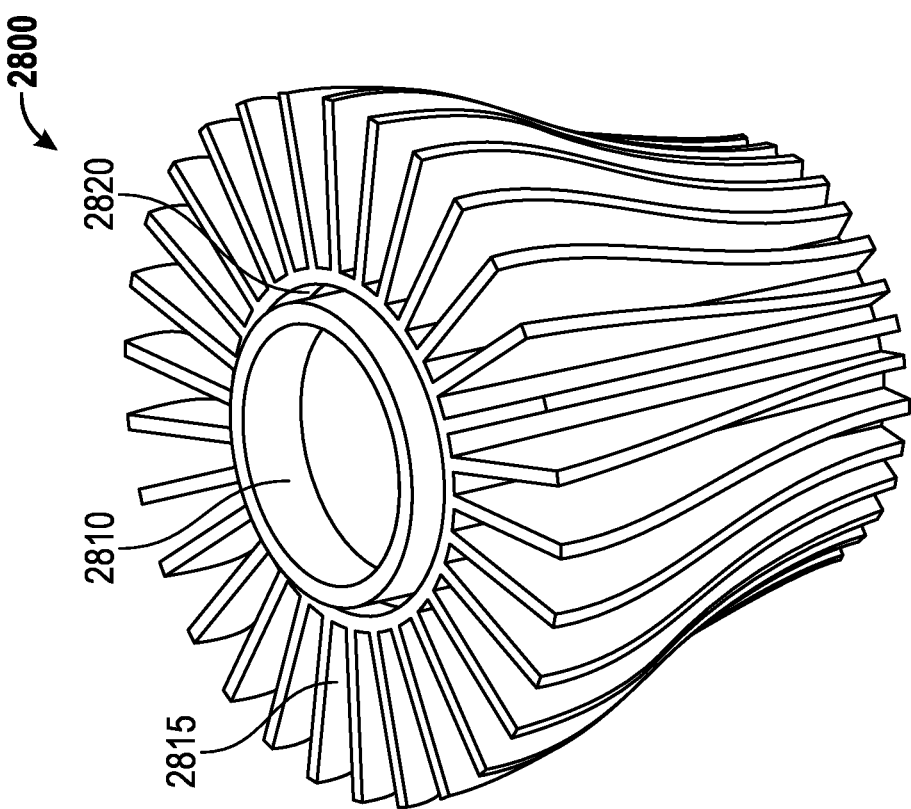
FIG. 28 is a perspective view of a further embodiment of a light emitting diode heat sink according to an example embodiment.

FIG. 28 is a perspective view of a further embodiment of a light emitting diode heat sink according to an example embodiment. In one embodiment, the heat sink core 2810 and heat sink fins 2815 may be formed from a single body. A light emitting diode package may be arranged within the heat sink core 2810, and the interior surface of the heat sink core 2810 may be reflective to direct light out of the heat sink core 2810. In one embodiment, a trough 2820 may be formed between the heat sink core 2810 and heat sink fins 2815 to secure a dome using adhesive, friction fit, snap fit, or other fastening method.

Figure 29:
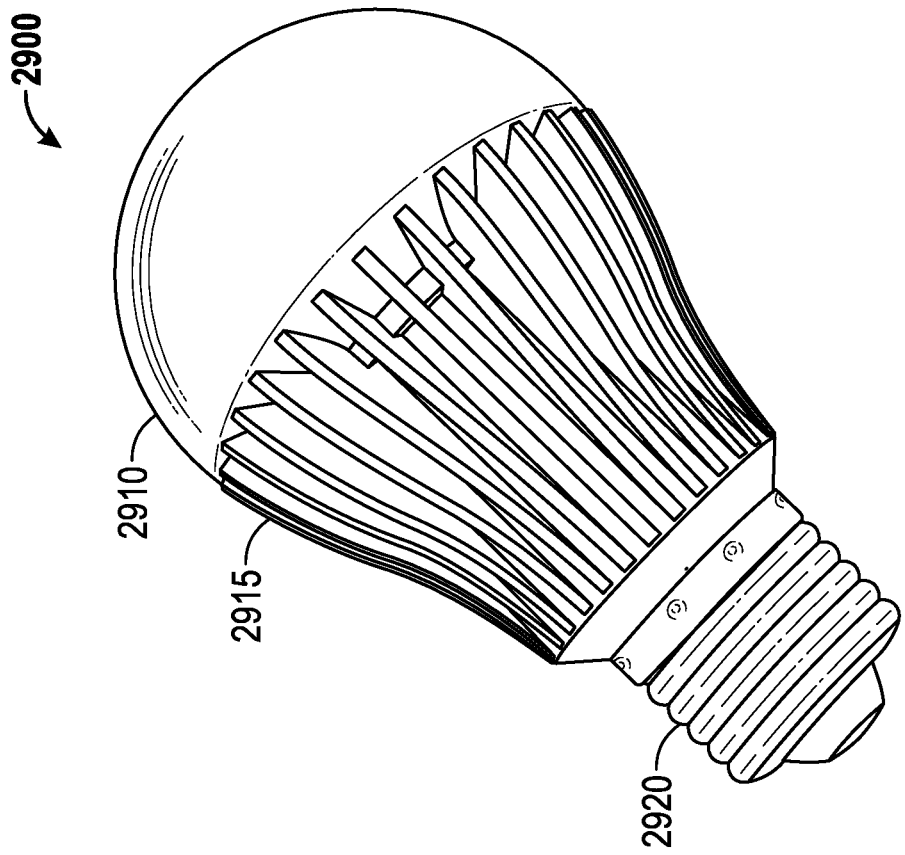
FIG. 29 is a perspective view of a further embodiment of an assembled light emitting diode based light bulb according to an example embodiment.

FIG. 29 is a perspective view of a further embodiment of an assembled light emitting diode based light bulb according to an example embodiment. The assembled light bulb may include a dome 2910, a heat sink 2915, and an Edison-style connector 2920. In one example embodiment, the heat sink fins extend radially further from the top of the tube, and then taper down to extend a similar radius out from the tube as the radius of the electronics module, creating shape similar to that of a common incandescent light bulb. In one embodiment, the heat sink 2915 may be formed of glass or reflective metal. The planar glass surfaces between the fins may reflect light from the light emitting diode, further enhancing the number of lumen per watt. In one embodiment, the dome 2910 may be adapted to snap fit to and over the heat sink. In one embodiment, the heat sink and fins may be formed of glass to provide strength, heat conduction, and low thermal expansion.

In one embodiment, a lens, and/or fins may or may not be included in the light bulb. Dome 2910 in this embodiment, as seen in FIG. 29, operates as a diffuser and may include Photocatalytic Titanium Dioxide. The Photocatalytic Titanium Dioxide may be sprayed on to an exterior of dome 2910 in one embodiment. In another embodiment, the Photocatalytic Titanium Dioxide may be mixed into molten plastic or other material while forming the dome 2910. In further embodiments, the diffuser 2910 may have Photocatalytic Titanium oxide sprayed, dipped or flowed onto or mixed into the diffuser. The dome may be made of GLASS, PMMA, POLYCARBONATE, ABS, or any polymer, that is transparent enough to let some light through.

Photocatalytic Titanium Dioxide, when exposed to UV or visual light, will act as a catalyst to react with air to create a hydroxyl, OH, radical or hydroxy group (—OH) that attacks microbes, bacteria, viruses, allergens and pollutants, which are decomposed producing by products that are less harmful, such as water, and CO2. LED's emit a visual light photons in the 400-500+ nm range. As such, the Photocatalytic Titanium Dioxide operates more efficiently as a photo catalyst to create OH, —OH, and O2 from ambient air as photons of visual light passes through the Titanium Dioxide. OH, —OH, and O2 may be lethal to bacteria, and other microbes, mold and organic pollutants. Ambient refers to an operating environment, which may be outdoors, indoors, in a controlled environment or other area where the LED based light bulb may operate that has suitable air contact for photocatalytic reaction which may occur when the light bulb is operating.

One or more dopants may be included in the Photocatalytic Titanium Dioxide, such as C, Cu, N, Sulfides and other metals and non-metals. In one embodiments, the Titanium Dioxide particles or crystals may be nano in size, which is 0.1 microns or smaller. Small nano particles, and crystals of photocatalytic Titanium Dioxide by volume have a larger surface area and are more efficient than larger particles as a photocatalyst. When sprayed on an outside, dipped, flowed on or infused into the bulb during manufacture of the bulb, nano particles, and crystals of Titanium Dioxide optimize the effectiveness of photocatalytic activity. The concentration of Titanium Dioxide particles may be adjusted based on the LED wattage, lumens produced, and other LED characteristics, and distance from the LED light source.

In one embodiment, the Titanium Dioxide may be formed in a peroxo titanic acid (PTA) solution by mixing titanic acid wet gel and hydrogen peroxide solution. The PTA solution may be a neutral, transparent, stable liquid that crystallizes to form an anatase phase after calcination at a temperature 250° C.-600 C in a crystallized form. When autoclaved at a temperature above 100° C. for 6 hours, the solution changes to a solution containing anatase crystals less than 20 nm in diameter. Aggregation of the crystals may occur after autoclaving at a temperature above 120° C. When heated to 100° C., the solution may be translucent and stable, containing anatase crystals approximate 9 nm in diameter.

Dip coating, spraying, flowing, over the LED diffuser and/or fixtures which will be proximate that LEDs in the solution may provide enhanced photocatalytic effect from light emitted in the visible spectrum, such as at least 400 nm to 500 nm or higher wavelength light. In further embodiments, a spray induction coupled plasma techniques or a spray combustion flame technique may be used to form the coating. The solution sprayed may be derived from $TiCl_4$ solution and transformed to a neutral translucent solution containing peroxo-modified anatase crystals by heating. Other known or yet to be discovered methods of creating stable Titanium Dioxide particles or crystals that may be applied in various ways to diffusers and fixtures may be used in further embodiments.

In one embodiment, the Titanium Dioxide coating may be formed using a method described in U.S. Pat. No. 6,602,918 by producing a titanium oxide-forming solution, wherein a hydrogen peroxide solution is added to a titanium-containing starting aqueous solution to form a peroxotitanium complex, a basic substance is then added to the peroxotitanium complex to obtain a solution which is in turn let stand or heated, thereby forming a precipitate of a peroxotitanium hydrate polymer, at least a dissolved component derived from the titanium-containing starting aqueous solution, except water, is then removed from the precipitate, and a hydroxide peroxide solution is finally allowed to act on a dissolved component-free precipitate. A dispersion with titanium dioxide may be dispersed therein to keep the Titanium Dioxide in suspension. The resulting nano sized crystalline structure may make the commercially available coating more photocatalytic such that the crystals stay in solution/suspension. In one embodiment, the solution is TPX 220 or TPX HL 220 available from Green Millennium in LA Calif. These solutions have a higher parts-per-million of crystals than many other solutions, which appear to have a higher photocatalytic reaction rate than lower concentration solutions. Note that lower concentration solutions will also work, but may not work as well. The solutions may also be applied by water fall (pouring it over the surface). A surfactant may be added to the solution to act as a wetting agent reduce surface tension allowing the coating to be uniform and avoid puddling.

Figure 31:
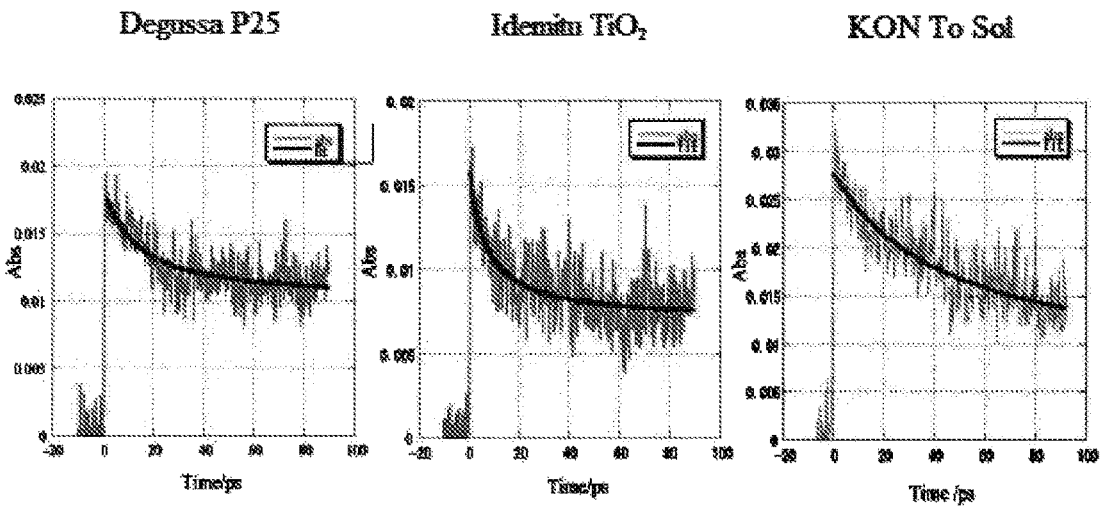
FIG. 31 is a series of graphs showing $TiO_2$ electron-hole recombination dynamics according to an example embodiment.

FIG. 31 is a series of graphs showing $TiO_2$ electron-hole recombination dynamics 3100. In some embodiments, higher photocatalytic activity occurs where electron-hole recombination becomes difficult. Graphs 3100 show a comparison of $TiO_2$ electron-hole recombination dynamics based on different solutions. An equation for determining $TiO_2$ electron-hole recombination rate is as follows:

$$[e]_t = \frac{[e]_0}{1 + [e]_0 k_r t} + BL$$

[e]$_0$=electron concentration at time zero
k$_r$=second order rate constant for electron-hole recombination
BL=baseline The smaller the rate constant (k$_r$), the more difficult for electron-hole recombination to occur, therefore higher photocatalytic activity is observed, such as shown in the following table:

TABLE

TiO$_2$ Electron-Hole Recombination Rate Constant Comparison

|  | P25 | PTA-sol | TO-sol | Idemitu |
|---|---|---|---|---|
| Kr (×10$^{32}$ cm$^3$s$^{-1}$) | 9.53 | 1.05 | 2.85 | 17.3 |

One example method of producing the titanium dioxide includes:

A 30% solution of hydrogen peroxide (20 ml) was added to and stirred with a solution (500 ml) of a 60% aqueous solution of titanium tetrachloride (5 ml) diluted with distilled water to prepare a transparent, brown solution. Ammonia water (1:9) was added dropwise to the solution to regulate the pH of the solution to 7, thereby preparing a transparent, yellow solution. The obtained solution was let stand at 25.degree. C. for a whole day and night to obtain yellow precipitates.

Distilled water was added to the precipitates after filtered and washed to prepare a solution (about 150 ml), and a cation exchange resin and an anion exchange resin, each in an amount of 25 g, were charged into the solution, which was then let stand for 30 minutes for removal of cationic and anionic substances.

An H$^{+1}$ substituted type resin obtained by treating Amberite IR120B (Na$^+$ substituted type, and made by Organo Co., Ltd.) with 2N hydrochloric acid for 1 hour was used for the cation ion exchange resin, and an OH$^-$ substituted type resin obtained by treating Amberite IRA410 (Cl$^-$ substituted type, and made by Organo Co., Ltd.) with 1N sodium hydroxide for 1 hour was used for the anion exchange resin.

Powders obtained by drying the resultant yellow precipitates at 25° C. were measured with an X-ray diffactometer (RAD-B made by Rigaku Denki Co., Ltd.) using a copper target while it was operated at an acceleration voltage of 30 kV and with a current of 15 mA. The obtained precipitates were found to be in an amorphous state.

On the other hand, the powders obtained by drying at 25° C. were mixed with potassium bromide to prepare a tablet. According to the potassium bromide tablet method, the tablet was then measured using a Fourier transform infrared absorption spectrometer (FT/IR-5300 made by Nippon Bunko Co., Ltd.) in combination with a transmission technique. Absorption was found in the vicinity of 900 cm$^{-1}$, indicating the presence of peroxo groups.

Then, the ion exchange resins were removed by filtration, and distilled water was added to prepare a solution (about 180 ml), which was in turn cooled with ice water. Thereafter, a 30% solution of hydrogen peroxide (20 ml) was added to the solution, followed by cooling. After the lapse of 1 hour, a transparent, yellow solution (200 ml) containing titanium was obtained.

After a one-month or longer storage in a refrigerator at 7° C., the solution remained unchanged. Five days after preparation, the pH of the transparent, yellow solution was 5.1. Powders obtained by drying this solution at normal temperature, too, were similarly measured by X-ray diffraction.

From the results of X-ray diffraction, it was found that the powders were in a noncrystalline state having no peak indicative of crystallinity. Results of a Fourier transform infrared spectroscopy resulted in absorption being found in the vicinity of 900 cm$^{-1}$, indicating the presence of a number of peroxo groups.

In one embodiment, prior to applying the Titanium oxide coating, a protection layer may applied to a diffuser. A fast-drying flat clear lacquer (such as Colormaster® flat crystal clear from Kyrylon, Inc) may be applied to the diffuser, or equivalent. The lacquer, which may be sprayed on the diffuser, may improve adhesion of the Titanium Dioxide coating. In one embodiment, the lacquer is applied to a plastic bulb exterior and/or interior in an even coating and may be sprayed. Applying the Titanium Dioxide directly to a plastic bulb may cause premature degradation of the plastic. A flat lacquer dries fast, which can improve manufacturing time by not having to wait as long for the protective coating to dry prior to applying the titanium dioxide containing solution. The flat lacquer identified above is stated to dry within 10 minutes of spraying but the drying time may be reduced with increased heat and airflow to a minute or less. Other materials that may be used for a protection layer include acetones, toluene, and polypropylene. Still other protection layer materials may be used that protect the diffuser/bulb from degrading.

If air can pass through the diffuser, the Titanium Dioxide coating and optional lacquer coating, may be applied to the inside of the diffuser in addition to or alternatively to coating the outside of the diffuser.

In a further embodiment, a visible organic material may be applied to the coated diffuser to demonstrate the photocatalytic operation of the coating. India ink may be used in one embodiment, and may be applied as visible spot on the diffuser. Any visible color of ink may be used, such as red, black, blue, or other color. With the coated bulb producing light, an observer can watch as the visible spot disappears. The spot may also take the shape of a design, such as a logo, or letters, or even the shape of a magnified bacteria.

Figure 30:
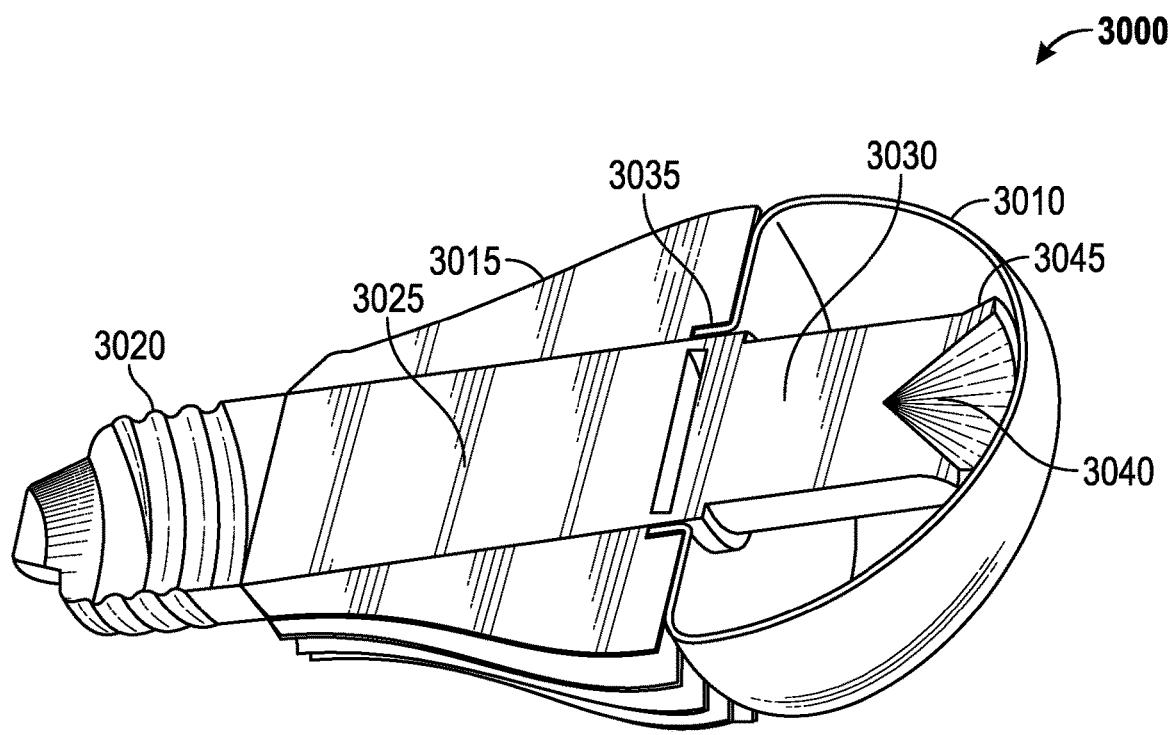
FIG. 30 is a perspective view of a cross-section of an assembled light emitting diode based light bulb according to an example embodiment.

FIG. 30 is a perspective view of a cross-section of an assembled light emitting diode based light bulb according to an example embodiment. The assembled light bulb may include a dome 3010, a heat sink 3015, an Edison-style connector 3020, a light emitting diode package 3025, and a lens 3030. The interior of the heat sink 3015 may be flush with most of the light emitting diode package 3025, and may include a gap 3035 to mount the dome 3010. A portion of the dome 3010 may be configured to be inserted into the gap 3035, and may be mounted to the heat sink 3015 and light emitting diode package 3025 using adhesive, friction fit, snap fit, or other fastening method. In one embodiment, the lens 3030 may direct light away from the light emitting diode package 3025 toward a divot 3040, where the divot 3040 disperses light about an angle of 360 degrees. In one embodiment, the lens 3030 may include a flared lens end 3045 to improve light dispersion. The flared lens end 3045 extends outside the nominal diameter of the lens 3030 in one embodiment such that light is reflected back toward the fins. The heat sink 3015 may include a reflective core or reflective fins, and the divot 3040 or the flared lens end 3045 may direct light toward the reflective heat sink 3015 to disperse light about an angle of 360 degrees. The lens 3030, divot 3040, and flared lens end 3045 may be formed using injection molding, or may be formed using precision glass molding or glass grinding and polishing.

To better illustrate the method and apparatuses disclosed herein, a non-limiting list of embodiments is provided here.

Example 1 is a device comprising: a light emitting diode package to emit visible light; an electronics module coupled to the light emitting diode package; and a dome having a coating containing Photocatalytic Titanium Dioxide optically coupled to the light emitting diode package such that the coating of Photocatalytic Titanium Dioxide acts as a photo-catalyst.

In Example 2, the subject matter of Example 1 optionally includes wherein the coating containing Photocatalytic Titanium Dioxide comprises crystallized Titanium Dioxide.

In Example 3, the subject matter of any one or more of Examples 1-2 optionally include wherein the coating further comprises a protective coating applied to the dome, wherein the Photocatalytic Titanium Dioxide is in a suspension applied to the protective coating.

In Example 4, the subject matter of Example 3 optionally includes wherein the dome comprises a plastic dome.

In Example 5, the subject matter of any one or more of Examples 1-4 optionally include wherein the coating further comprises a coating of lacquer applied to the dome, wherein the Photocatalytic Titanium Dioxide is in a suspension applied to the coating of lacquer.

In Example 6, the subject matter of Example 5 optionally includes wherein the lacquer comprises a clear lacquer.

In Example 7, the subject matter of Example 6 optionally includes wherein the lacquer comprises a flat clear lacquer.

In Example 8, the subject matter of any one or more of Examples 1-7 optionally include wherein the Titanium Dioxide is photocatalytic in human visible light.

In Example 9, the subject matter of any one or more of Examples 1-8 optionally include 400 nm or longer wavelength light.

In Example 10, the subject matter of any one or more of Examples 1-9 optionally include 500 nm or longer wavelength light.

In Example 11, the subject matter of any one or more of Examples 1-10 optionally include and further comprising a fixture at least partially exposed to light when emitted from the light emitting diode package, the fixture having a layer containing Photocatalytic Titanium Dioxide exposed to the light emitted.

In Example 12, the subject matter of any one or more of Examples 1-11 optionally include and further comprising an organic material spot supported by the dome.

In Example 13, the subject matter of Example 12 optionally includes wherein the organic material spot comprises India ink.

Example 14 is a device comprising: a light emitting diode package to emit visible light; an electronics module coupled to the light emitting diode package; and a diffuser having a coating containing Titanium Dioxide optically coupled to the light emitting diode package such that the coating of Titanium Dioxide acts as a photo-catalyst.

In Example 15, the subject matter of Example 14 optionally includes wherein the coating containing Titanium Dioxide comprises a layer of crystallized Titanium Dioxide applied to an outer surface of the diffuser.

In Example 16, the subject matter of any one or more of Examples 14-15 optionally include wherein the coating further comprises a coating of lacquer applied to the diffuser, wherein the Titanium Dioxide is in a suspension applied to the coating of lacquer.

In Example 17, the subject matter of Example 16 optionally includes wherein the lacquer comprises a clear lacquer.

In Example 18, the subject matter of Example 17 optionally includes wherein the lacquer comprises a flat lacquer.

In Example 19, the subject matter of any one or more of Examples 14-18 optionally include wherein the titanium oxide is photocatalytic in human visible light.

In Example 20, the subject matter of any one or more of Examples 14-19 optionally include 400 nm or longer wavelength light.

In Example 21, the subject matter of any one or more of Examples 14-20 optionally include 500 nm or longer wavelength light.

In Example 22, the subject matter of any one or more of Examples 14-21 optionally include and further comprising a fixture at least partially exposed to light when emitted from the light emitting diode package, the fixture having a layer containing Titanium Dioxide exposed to the light emitted.

Example 23 is a device comprising: a light emitting diode package to emit visible light; an electronics module coupled to the light emitting diode package; a diffuser optically coupled to diffuse the emitted visible light; a fixture coupled to support the light emitting diode package; and at least one of the diffuser and fixture having a coating containing Titanium Dioxide particles or crystals, optically coupled to the light emitting diode package such that the coating containing Titanium Dioxide acts as a photocatalyst.

In Example 24, the subject matter of Example 23 optionally includes wherein the coating containing Titanium Dioxide particles comprises crystallized Titanium Dioxide.

In Example 25, the subject matter of any one or more of Examples 23-24 optionally include wherein the coating further comprises a coating of lacquer applied to at least one of the diffuser and fixture, wherein the Titanium Dioxide is in a suspension applied to the coating of lacquer.

In Example 26, the subject matter of Example 25 optionally includes wherein the lacquer comprises a clear lacquer.

In Example 27, the subject matter of Example 26 optionally includes wherein the lacquer comprises a flat clear lacquer.

In Example 28, the subject matter of any one or more of Examples 23-27 optionally include wherein the Titanium Dioxide is photocatalytic in human visible light.

In Example 29, the subject matter of any one or more of Examples 23-28 optionally include 400 nm or longer wavelength light.

In Example 30, the subject matter of any one or more of Examples 23-29 optionally include 500 nm or longer wavelength light.

Example 31 is a method comprising: coupling a light emitting diode package to emit visible light to an electronics module and a diffuser optically coupled to diffuse the emitted visible light; and forming a coating containing Titanium Dioxide on the diffuser optically coupled to the light emitting diode package such that the coating containing Titanium Dioxide acts as a photo-catalyst.

In Example 32, the subject matter of Example 31 optionally includes and further comprising forming the layer with a first layer of lacquer supported by the diffuser.

Example 33 is a method comprising: coupling a light emitting diode (LED) package to emit visible light to an electronics module, a diffuser optically coupled to diffuse the emitted visible light, and a fixture coupled to support the light emitting diode package; and forming a coating containing Titanium Dioxide crystals exposed to ambient air and optically coupled to the light emitting diode package such that the coating containing Titanium Dioxide acts as a photo-catalyst.

In Example 34, the subject matter of Example 33 optionally includes and further comprising forming the layer with a first layer of lacquer supported by the LED diffuser, bulb, tube, or fixture.

In Example 35, the subject matter of any one or more of Examples 33-34 optionally include and further comprising forming an organic material containing visible spot supported by the diffuser.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

What is claimed is:

1. A device comprising:
   a light emitting diode package to emit human visible light to light an area;
   an electronics module coupled to the light emitting diode package; and
   a dome having a coating containing Photocatalytic Titanium Dioxide optically coupled to the light emitting diode package such that the coating of Photocatalytic Titanium Dioxide acts as a photo-catalyst in response to the human visible light emitted by the light emitting diode package, wherein the coating further comprises a protective coating applied to the dome, wherein the Photocatalytic Titanium Dioxide is in a suspension applied to the protective coating.

2. The device of claim 1 wherein the coating containing Photocatalytic Titanium Dioxide comprises crystallized Titanium Dioxide that acts as a photo-catalyst in response to light having a wavelength of 500 nm or higher.

3. The device of claim 1 wherein the dome comprises a plastic dome.

4. The device of claim 1 wherein the coating further comprises a coating of lacquer applied to the dome, wherein the Photocatalytic Titanium Dioxide is in a suspension applied to the coating of lacquer.

5. The device of claim 4 wherein the lacquer comprises a clear lacquer.

6. The device of claim 1 wherein the Titanium Dioxide is photocatalytic in human visible light having a wavelength of 500 nm or higher.

7. The device of claim 1 and further comprising a fixture at least partially exposed to light when emitted from the light emitting diode package, the fixture having a layer containing Photocatalytic Titanium Dioxide exposed to the light emitted.

8. The device of claim 1 and further comprising a visible organic material spot supported by the dome coating configured to visibly demonstrate the photo-catalyst response of the coating.

9. The device of claim 8 wherein the organic material spot comprises India ink.

10. A device comprising:
    a light emitting diode package to emit human visible light to light an area;
    an electronics module coupled to the light emitting diode package;
    a diffuser optically coupled to diffuse the emitted visible light;
    a fixture coupled to support the light emitting diode package; and
    at least one of the diffuser and fixture having a coating containing Titanium Dioxide particles or crystals, optically coupled to the light emitting diode package such that the coating containing Titanium Dioxide acts as a photocatalyst in response to the human visible light emitted by the light emitting diode package, wherein the coating further comprises a protective coating applied to the dome, wherein the Titanium Dioxide is in a suspension applied to the protective coating.

11. The device of claim 10 wherein the coating containing Titanium Dioxide particles comprises crystallized Titanium Dioxide.

12. The device of claim 10 wherein the protective coating further comprises a coating of lacquer.

13. The device of claim 12 wherein the lacquer comprises a clear lacquer.

14. The device of claim 13 wherein the lacquer comprises a flat clear lacquer.

15. The device of claim 10 wherein the Titanium Dioxide coating is photocatalytic in human visible light having a wavelength of 500 nm or higher.

16. The device of claim 10 wherein the Titanium Dioxide is photocatalytic at 500 nm or longer wavelength light.

17. A method comprising:
    coupling a light emitting diode (LED) package to emit human visible light to light an area to an electronics module, a diffuser optically coupled to diffuse the emitted visible light, and a fixture coupled to support the light emitting diode package; and
    forming a coating containing Titanium Dioxide crystals exposed to ambient air and optically coupled to the light emitting diode package such that the coating containing Titanium Dioxide acts as a photo-catalyst in response to the human visible light emitted by the LED package, wherein the coating further comprises a coating applied to the diffuser, wherein the Titanium Dioxide is in a suspension applied to the coating.

18. The method of claim 17 wherein the coating comprises a first layer of lacquer supported by the LED diffuser, bulb, tube, or fixture.

19. The method of claim 17 and further comprising forming an organic material containing visible spot supported by the diffuser to visibly demonstrate the photo-catalyst response of the coating.

* * * * *